United States Patent [19]

Veech

[11] Patent Number: 5,091,094
[45] Date of Patent: Feb. 25, 1992

[54] HEMODIALYSIS PROCESSES & HEMODIALYSIS SOLUTIONS

[76] Inventor: Richard L. Veech, 712 Brent Rd., Rockville, Md. 20850

[21] Appl. No.: 240,386

[22] Filed: Aug. 30, 1988

Related U.S. Application Data

[60] Continuation of Ser. No. 866,480, May 23, 1986, abandoned, which is a division of Ser. No. 748,184, Jun. 24, 1985, Pat. No. 4,668,400.

[51] Int. Cl.⁵ .............................................. B01D 61/32
[52] U.S. Cl. .................................... 210/647; 210/96.2; 210/321.71
[58] Field of Search ................. 210/321.71, 96.2, 647, 210/94; 128/630

[56] References Cited

U.S. PATENT DOCUMENTS

| | | | |
|---|---|---|---|
| 3,962,075 | 6/1976 | Fialkoff | 210/647 X |
| 4,202,760 | 5/1980 | Storey et al. | 210/647 X |
| 4,231,871 | 11/1980 | Lipps et al. | 210/321.3 X |
| 4,370,983 | 2/1983 | Lichtenstein | 128/630 |
| 4,386,634 | 6/1983 | Stasz et al. | 222/386.5 |
| 4,404,192 | 9/1983 | Suzuki | 424/153 |
| 4,469,593 | 9/1984 | Ishihara et al. | 210/96.2 |
| 4,508,622 | 4/1985 | Polaschegg et al. | 210/321.71 X |
| 4,508,622 | 4/1985 | Pulaschegg et al. | 210/96.2 |
| 4,601,830 | 7/1986 | Chen | 210/647 |
| 4,661,246 | 4/1987 | Ash | 210/94 X |

*Primary Examiner*—Frank Spear
*Attorney, Agent, or Firm*—Hill, Van Santen, Steadman & Simpson

[57] ABSTRACT

Techniques for predicting the respective concentrations and distributions of diffusible materials in solutions on opposing sides of a semi permeable membrane are provided. Unique compositions for hemodialysis using the mathematical relationships involved are provided. Also processes are provided for controlling the rate of change in concentration of a diffusible material in and fluid into another fluid on an opposing side of semipermeable membrane are provided. Apparatus for practicing such processes are described.

16 Claims, 13 Drawing Sheets

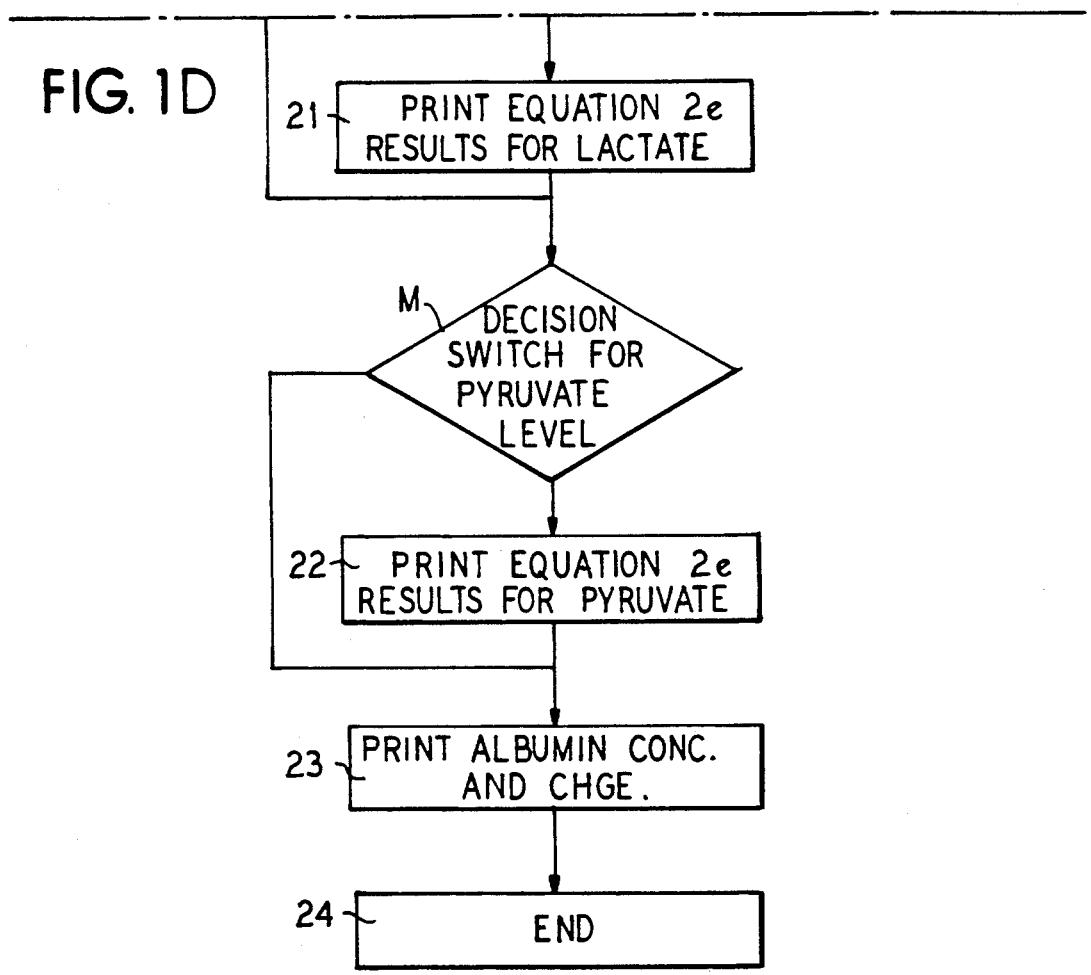

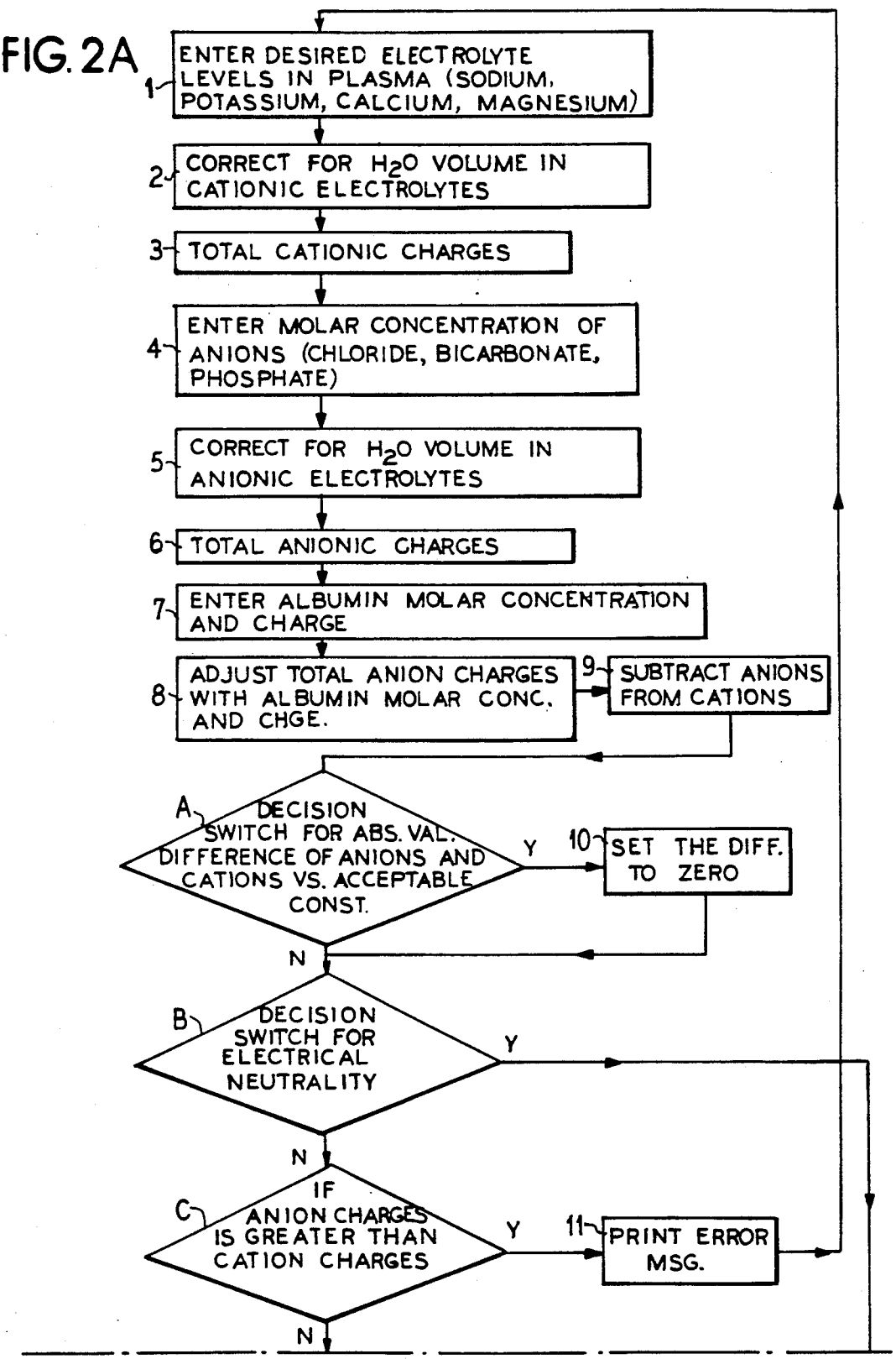

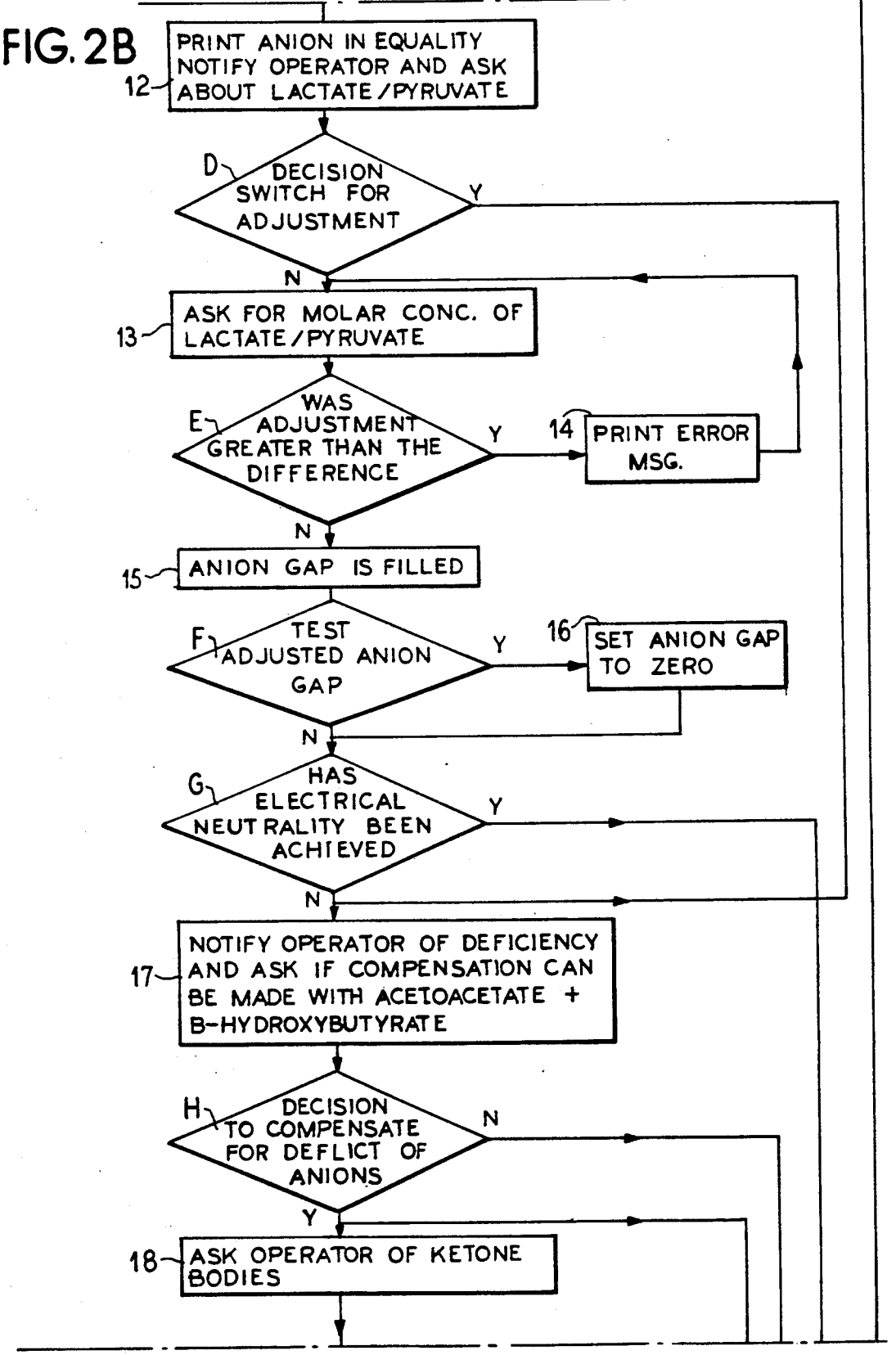

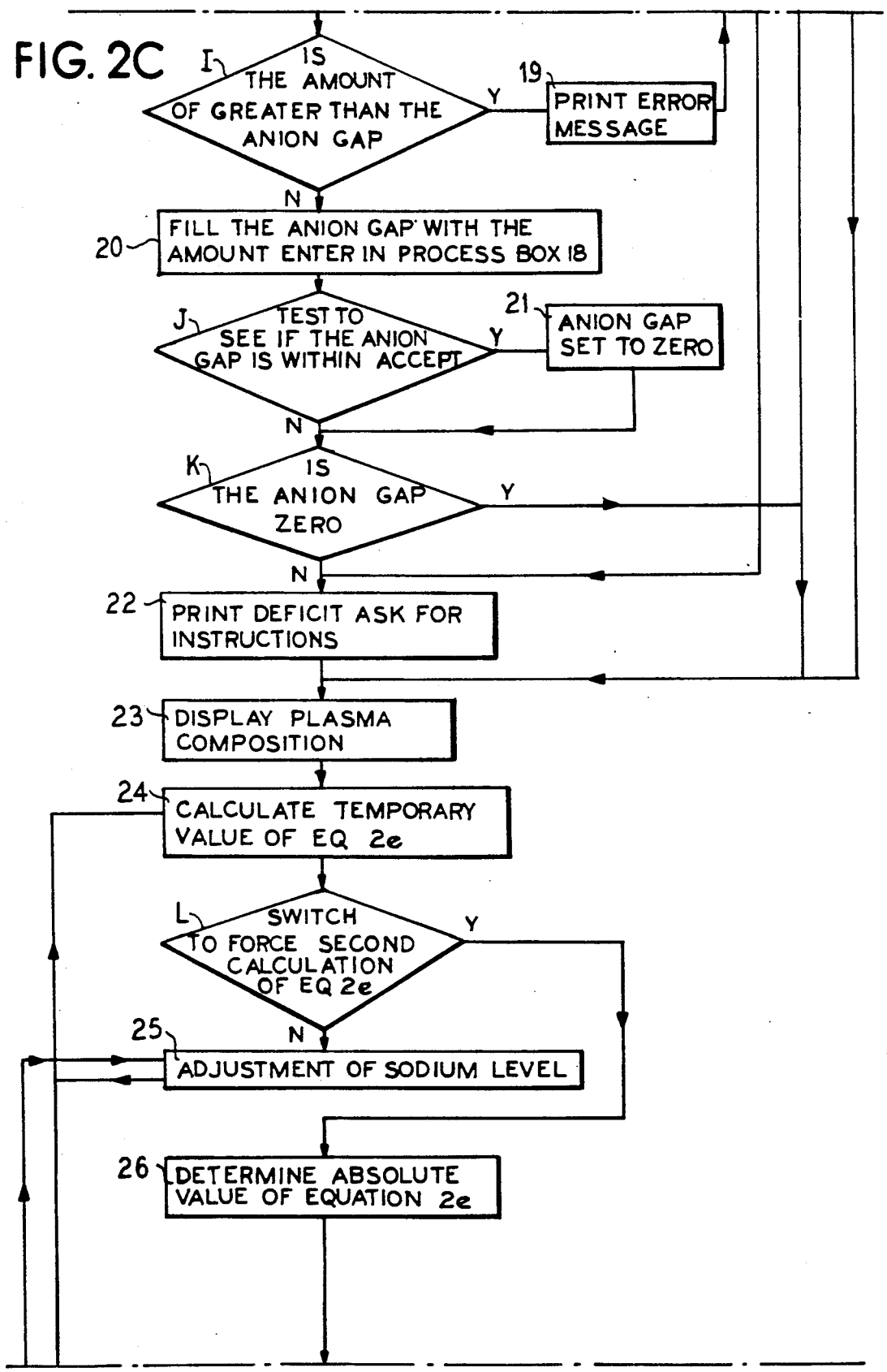

FIG. 2F

38 — PRINT PYRUVATE DETAIL

↓

WAS AMOUNT OF ACETOACETATE AND β-HYDROXYBUTYRATE = 0
- V / Y

N ↓

39 — PRINT β-HYDROXYBUTYRATE DETAIL

↓

40 — PRINT ACETOACETATE DETAIL

↓

HAS THE ANION GAP BEEN FILLED
- W / Y

N ↓

41 — PRINT VARIABLE ELEMENT TO FILL ANION GAP AND THE VALUE OF THE GAP

↓

42 — PRINT PLASMA ALBUMIN CONC AND CHAGE

↓

43 — END

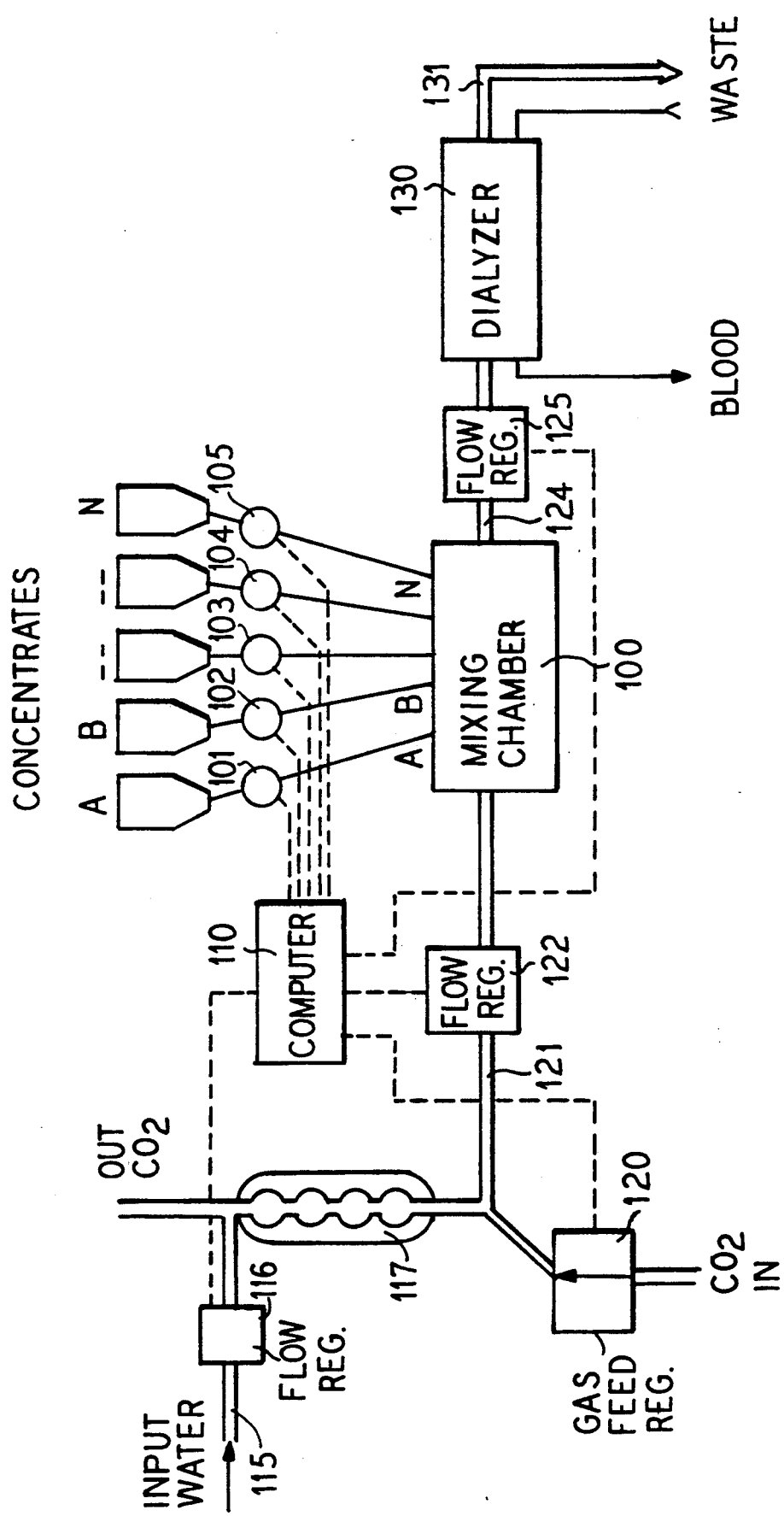

HEMODIALYSIS PROCESSES & HEMODIALYSIS SOLUTIONS

This application is a continuation of application, Ser. No. 06/866,480 filed May 23, 1986, now abandoned, which was, in turn, a Division of application Ser. No. 06/748,184 filed June 24, 1985, now U.S. Pat. No. 4,668,400.

BACKGROUND OF INVENTION

1. Field of The Invention

This invention lies in the field of techniques and compositions for hemodialysis and related matters.

2. State of the Art

The vital functions of highly developed organisms are closely dependent on the internal aqueous medium and on the maintenance in it of extreme constancy of chemical and physical properties.

It has long been recognized that all animal intracellular and extracellular body fluids contain inorganic electrolytes, and that these electrolytes are involved in, and profoundly influence, various life processes. Attempts to make artificial electrolyte fluids which may bathe tissues or be administered to the human blood stream have been known since about 1880, and, although modern analytical tools and procedures have clarified compositional details of blood electrolytes, the use of various aqueous electrolytes solutions for in vivo purposes in human medicine and related fields has been extant for approximately one hundred years.

Those inorganic electrolytes characteristically found in normal human blood serum at respective concentration levels above about 1 millimolar per liter of concentration are shown below in Table 1. Also, for comparative purposes, in Table II are shown some representative compositions of various aqueous electrolyte solutions that have been previously prepared and used for in vivo (including dialysis) purposes. In general, the philosophy behind the formulation of aqueous electrolyte solutions for in vivo use has been that such should mimic or closely resemble the chemical composition of electrolytes in blood and plasma.

An electrolyte is a substance (usually a salt, acid or base) which in solution dissociates wholly or partly into electrically charged particles known as ions (the term is also sometimes used in the art to denote the solution itself, which has a higher electrical conductivity than the pure solvent, e.g. water). The positively charged ions are termed cations while the negatively charged ions are termed anions. Strong and weak electrolytes are recognized. The dissociation of electrolytes is very markedly dependent on concentration; it increases with increasing dilution of the solutions. Because of dissociation considerations, the term "sigma" or the greek letter for sigma ("Σ") is sometimes employed herein as a prefix to designate the total presence of a specified material, such as an electrolyte, whether or not all of the material is in an ionic form complexed with a heavy metal, or regardless of charge on the material in a given solution. A pair of brackets ([]) indicates the free concentration of the substance indicated as opposed to that bound to tissue components, such as proteins.

TABLE 1

Chemical Content of the Millimolar Components of Normal Human Blood Serum.
(From N Eng J Med 1970; 283: 1276-1285)
Values are given as ranges in units of m moles/L serum, mEq/L serum, or mEq/L serum $H_2O$

| Cations | m mol/L serum | mEq/L serum | mEq/L serum $H_2O$ (assuming 935 ml $H_2O$/L serum) |
|---|---|---|---|
| $Na^+$ | 136–145 | 136–145 | 145–155 |
| $K^+$ | 3.5–5.0 | 3.5–5.0 | 3.7–5.3 |
| $Ca_{total}$ | 2.1–2.6 | — | — |
| free $[Ca^{2+}]$[1] | [1.065] | [2.12] | [2.12] |
|  | 0.035 | 0.07 | 0.0.7 |
| $Mg_{total}$ | 0.75–1.25 | — | — |
| free $[Mg^{2+}]$[2] | [0.53] | [1.06] | [1.06] |
| Total mEq Cations |  | 142.7–153.2 | 152.6–163.8 |
| Total mOsmoles | 141–151.6 |  |  |
| Anions |  |  |  |
| $Cl^-$ | 100–106 | 100–106 | 107–113 |
| $HCO_3^-$ | 26–28 | 26–28 | 27.8–29.9 |
| $\Sigma\ Pi^{1.8-}$ | 1–1.45 | 1.8–2.6 | 1.9–2.8 |
| $\Sigma\ SO_4^{2-}$ | 0.32–0.94 | 0.32–0.94 | 0.34–1.0 |
| Metabolic acids$^-$[3] | *2.0–4.0 | *2.0–4.0 | *2.1–4.3 |
| Apparent Total mEq Anions |  | 130–141.5 | 139.1–151 |
| Total mOsmoles | 141–151.6 |  |  |
| Apparent Anion Gap |  | 12.7–11.7 | 11.7–11.1 |
| Polyanions |  |  |  |
| $Albumin^{20-}$[4] | 0.58–0.73 | 11.8–14.8 | 12.6–15.8 |
| Ca—Mg $Albuminate^{17.7-}$[5] | 0.58–0.73 | 10.3–12.9 | 11.0–13.7 |
| Non Ionics (fasting) | 3.9–5.6 |  |  |
| Glucose (fed)[6] | 7–11 |  |  |
| Urea (5–25 mg %) | 2.9–8.9 |  |  |
| Globulins (3 g %) | *0.2 |  |  |
| $CO_2 + H_2CO_3$ | 0.99–1.39 |  |  |
| Grand Total mOsmoles | 279–314 |  |  |
| Total mEq Cations |  | 142.7–153.7 | 152.6–163.8 |

TABLE 1-continued

Chemical Content of the Millimolar Components of Normal Human Blood Serum.
(From N Eng J Med 1970; 283: 1276–1285)
Values are given as ranges in units of m moles/L serum, mEq/L serum, or mEq/L serum $H_2O$

| Cations | m mol/L serum | mEq/L serum | mEq/L serum $H_2O$ (assuming 935 ml $H_2O$/L serum) |
|---|---|---|---|
| Total mEq Anions | | 140.3–154.4 | 150.0–165.1 |

[1]Free [$Ca^{2+}$] from Burritt M F, Pierides A M, Offord k P. Mayo Clin Proc 55, 606–613, 1980.
[2]Free [$Mg^{2+}$] from Walser M. J Clin Invest 40, 723, 1961
[3]Range of major metabolic acids above 0.1 ∂M are l-lactate, pyruvate, acetoacetate, c-a hydroxybutyrate. - Veech R L unpub.
[4]The charge on albumin at pH 7.365 in 0.15 M NaCl is −20.5. Tanford C. J Am Chem Soc 72, 441–451, 1950)
[5]Considering the binding constants of albumin for $Ca^{2+}$ and $Mg^{2+}$, the charge on albumin in serum may be estimated to be between 17–18. (See Veloso D, Oskarson M A, Guynn R, Veech R L. J Biol Chem 248, 4811–4819, 1973.
[6]Fed glucose values are from Veech R L. Unpublished observations.

Contemporarily, a large number of different aqueous electrolyte solutions are prepared, sold in commerce, and used as in vivo fluids, including dialysis (both hemo- and peritoneal).

In the original hemodialysis solutions, attempts were made to duplicate Krebs-Henseleit as Table II shows. These original hemodialysis systems were open however and loss of $CO_2$ lead to precipitation of Ca as $CaCO_3$. The original dialysis solutions contained excessive $Cl^-$ ion in excess of $Na^+$ to overcome the "anion gap". The term "anion gap" is used to connote the difference in milliequivalents/liter between the apparent sum of routinely measured inorganic cations in plasma and the apparent sum of routinely measured inorganic anions in plasma. The law of electrical neutrality of solutions states that such a term has no real physical meaning, but the term is widely used and accepted.

In 1949, the use of high concentrations of acetate as a metabolizable organic anion was advocated (Mudge, G. H., Mannining, J. A., Gilman, A. Proc. Soc. Exptl. Biol. Med. 71, 136–138, 1949). This idea led in 1964 to the advocacy of the use of 35–45 mM (millimolar) acetate in commercial hemodialysis fluids (Mion, C. M., Hegstrom, R. M., Boen, S. T., Scribner, B. H. Trans. Am. Soc. Artif. Internal Organs 10, 110–113, 1964).

In 1981, (Bjaelder, Nephron 27, 142–145, 1981) advocated that use of 38.6 mM acetate instead of 32.6 mM acetate on the grounds that "acetate" represented an equivalent to bicarbonate. Bjaelder showed that the use of 32.6 mM acetate in hemodialysis left patients in chronic acidosis while 38.6 mM acetate did not. He cites the difference in acetate concentration as the cause.

TABLE II

Prior Art Hemodialysis Fluids. For recent discussion see Parsons FM, Stewart WK. Composition of Dialysis Fluid. In: Replacement of Renal Function by Dialysis (Drucker W, Parsons FM, Maher JP, eds.) Martinus Nijhoff, Hingham, pp 148–170, 1983.

| Units mmoles L fluid | Normal Plasma N.E.J.H. 283, 1285 1970 | 2d6 Kolff 1947 | 2d7 Brigham 1952 | 2a16 Scribner's Acetate 1964 | 2a17 Commercial Acetate 1981 | 2a18 Bjaelder "Low" Acet. 1981 | 2a19 Bjaelder "High" Acet. 1981 | 2b2 Kraut $HCO_3$-Acetic Acid, 1981 | 2b3 COBE $HCO_3$-Acetic Acid |
|---|---|---|---|---|---|---|---|---|---|
| Na | 136–145 | 126 | 140 | 135 | 140 | 134 | 136 | 140 | 135 |
| K | 3.5–5.0 | 5.6 | 4 | 1.5 | 2 | 2.2 | 2.2 | 2 | 2 |
| Ca | 2.1–2.6 | 1.0 | 1.25 | 1.25 | 0.875 | 1.84 | 1.91 | 1.75 | 1.5 |
| free [$Ca^{2+}$] | [1.06] | | | | | | | | |
| Mg | 0.75–1.25 | | 0.5 | 0.5 | 0.375 | 0 | 0 | — | 0.375 |
| free [$Mg^{2+}$] | [0.53] | | | | | | | | |
| mEq Cations | 142.7–153.2 | 133.6 | 147.5 | 140 | 144.5 | 139.88 | 142.02 | 145.5 | 140.75 |
| Cl | 100–106 | 109 | 120.7 | 105 | 106 | 107.28 | 103.82 | 107 | 106.5 |
| $HCO_3$ | 26–28 | 23.9 | 26.8 | | | | | 33 | 33 |
| Pi | 1–1.45 | | | | | | | | |
| $SO_4$ | 0.32–0.94 | | | | | | | | |
| L-lactate | 0.6–1.8 | | | | | | | | |
| pyruvate | | | | | | | | | |
| Lact/pyr | | | | | | | | | |
| D B OH-butyrate | | | | | | | | | |
| aceto-acetate | | | | | | | | | |
| B HB/ acac | | | | | | | | | |
| acetate | | | | 35 | 38.5 | 32.6 | 38.2 | | |
| Other | | | | | | | | 2 HAcetate ?3.5 gluconate | 2 HAcetate |
| mEq anions | 128.7–139.4 | 132.9 | 147.5 | 140 | 144.5 | 139.88 | 142.02 | 145.5 | 141.5 |
| Na/Cl | 1.28–1.45 | 1.16 | 1.16 | 1.29 | 1.32 | 1.25 | 1.31 | 1.31 | 1.27 |
| Glucose or others | 3.9–5.6 | 76–151 | 10 | 0 | 0 | 0 | 0 | 0 | 0 |

TABLE II-continued

Prior Art Hemodialysis Fluids. For recent discussion see Parsons FM, Stewart WK. Composition of Dialysis Fluid. In: Replacement of Renal Function by Dialysis (Drucker W, Parsons FM, Maher JP, eds.) Martinus Nijhoff, Hingham, pp 148-170, 1983.

| | | | | | | | | | |
|---|---|---|---|---|---|---|---|---|---|
| $CO_2$ | 0.99-1.39 | 0 | 1.24 | 0 | 0 | 0 | 0 | ~1.3 | ~1.3 |
| pH | 7.35-7.45 | ~8.6 | 7.4 | ~5.5-6.5 | ~5.5-6.5 | ~6.7 | ~6.7 | ~7.4 | ~7.4 |
| mOsm | 285-295 | 343-418 | 304.8 | 278.25 | 287.75 | 277.92 | 282.97 | 289.3 | 280.4 |

2d6 Kolff W J. New Ways of Treating Uremia, J&A Churchill, London, 1947
2d7 Murphy W P, Swan R C, Walter C, Weller J M, Merrill J P. J Lab Clin Med 40: 436, 1952. Essentially Krebs Henseleit, but with lower Mg and Ca.
2a16 Mion C M, Hegstrom R M, Boen S T, Scribner B H. Trans Am Soc Artif intern Organs 10: 110-113, 1964
2a17 Made in concentrates by numerous manufactures. The mean concentrations used are given in 2d17 according to Parsons F M and Stewart W K, listed above in title.
2a18 Bjaelder et al Nephron 27: 142-145, 1981. "Low" acetate leaves the patients acidotic, "high" acetate leaves them in normal. Bjaelder's interpretation for the reasons for the acidosis are incorrect.
2b6 Kraut J et al. Clin Neph 15: 181, 1981. Used $HCO_3$ and acetic acid.
2b3 Commercial source. COBE Laboratories, 1201 Oak Street, Lakewood Colorado.

As we will show here, the reason "high acetate" corrects acidosis is that the Na:Cl ratio in Bjaelder's fluid was 1.31 in the high acetate and 1.25 in low acetate. Bjaelder or clinicians in general were unaware of the importance of this. Nevertheless, many clinical observations have suggested acetate dialysis leads to numerable complications as recent editorials in the *British Med. J.* 287, 308-309, 1983 questioning the use of acetate dialysis indicate. However until now, no reasonable alternative to acetate dialysis has been devised, nor have the physical chemical and metabolic laws governing dialysis been clearly presented.

In addition to acetate and $HCO_3^-$, the current reference work "Facts and Comparisons" indicates various commercial peritoneal dialysis fluids which contain dl-lactate anion. (Table III)

All of the prior art dialysis solutions (with or without nutrients) as exemplified in Table II and III are now believed to lead to undesirable and pathological consequences particularly through extended usage.

In addition to failing to solve the anion gap problem (or to provide a normal milliequivalent ratio of sodium cation to chloride anions) without causing profound and adverse physiological effects (including disruption of normal redox state and normal phosphorylation potential), many prior art aqueous electrolyte solutions for in vivo usage fail to have a pH which approximates the pH of mammalian intracellular and extracellular fluids, especially plasma or serum.

TABLE III

Prior Art Peritoneal Dialysis Solutions
The compilation of solutions are taken from: Facts and Comparisons J. B. Lippincott, 111 West Port Plaza, Suite 423, St Louis, Mo. 63146, October, 1982, p. 705-706.
Indication: Acute renal failure or exacerbation of chronic renal failure; acute poisoning by dialyzable toxins; acute pulmonary edema; intractable peripheral edema; anasarca; endogenous intoxication such as hyperkalemia, hyperuricemia, hypercalcemia, and uremia; hepatic coma, especially with hepatorenal syndrome.

| Product and Distributor | Dextrose g/liter | Electrolyte content given in mEq/liter | | | | | | | Osmolarity mOsm/liter | How Supplied |
|---|---|---|---|---|---|---|---|---|---|---|
| | | $Na^+$ | $K^+$ | $Ca^{++}$ | $Mg^{++}$ | $Cl^-$ | Lactate | Acetate | | |
| Dianeal w/1.5% Dextrose (Travenol) | 15 | 141 | | 3.5 | 1.5 | 101 | 45 | | 366 | In 1000 and 2000 ml. |
| Dianeal PD-2 w/1.5% Dextrose (Travenol) | 15 | 132 | | 3.5 | 0.5 | 96 | 40 | | 346 | In 2000 ml. |
| Dianeal 137 w/1.5% Dextrose (Travenol) | 15 | 132 | | 3.5 | 1.5 | 102 | 35 | | 347 | In 2000 ml. |
| Inpersol w/1.5% Dextrose (Abbott) | 15 | 132 | | 3.5 | 1.5 | 99 | 35 | | 344 | In 1000 and 2000 ml. |
| Peridial 1½-D (Cutter) | 15 | 133 | | 3.5 | 1.5 | 102 | 35 | | 348 | In 1000 and 2000 ml. |
| Peritoneal Dialysis w/1.5% Dextrose-Low Sodium (American-McGaw) | 15 | 131 | | 3.4 | 1.5 | 100 | 35 | | 345 | In 1000 and 2000 ml. |
| Dianeal K w/1.5% Dextrose (Travenol) | 15 | 141 | 4 | 3.5 | 1.5 | 105 | 45 | | 374 | In 1000 ml. |
| Dianeal K-141 w/1.5% Dextrose (Travenol) | 15 | 132 | 4 | 3.5 | 1.5 | 106 | 35 | | 355 | In 2000 ml. |
| Peritoneal Dialysis w/1.5% Dextrose-Potassium (American McGaw) | 15 | 140 | 4 | 4.0 | 1.5 | 105 | | 45 | 375 | In 2000 ml. |
| Peritoneal Dialysis w/1.5% Dextrose (American McGaw) | 15 | 141 | | 4.0 | 1.5 | 103 | | 45 | 370 | In 1000 and 2000 ml. |
| Dianeal PD-2 w/2.5% Dextrose (Travenol) | 25 | 132 | | 3.5 | 0.5 | 96 | 40 | | 396 | In 2000 ml. |
| Dianeal PD-2 w/4.25% Dextrose (Travenol) | 42.5 | 132 | | 3.5 | 0.5 | 96 | 40 | | 485 | In 2000 ml. |
| Dianeal w/4.25% Dextrose (Travenol) | 42.5 | 141 | | 3.5 | 1.5 | 101 | 45 | | 505 | In 2000 ml. |
| Dianeal 137 w/4.25% Dextrose (Travenol) | 42.5 | 132 | | 3.5 | 1.5 | 102 | 35 | | 486 | In 2000 ml. |
| Inpersol w/4.25% Dextrose (Abbott) | 42.5 | 132 | | 3.5 | 1.5 | 99 | 35 | | 484 | In 2000 ml. |
| Peridial 4½-D (Cutter) | 42.5 | 133 | | 3.5 | 1.5 | 102 | 35 | | 487 | In 2000 ml. |
| Peritoneal Dialysis w/4.25% Dextrose-Low Sodium (American McGaw) | 42.5 | 131.5 | | 3.4 | 1.5 | 100 | 35 | | 485 | In 2000 ml. |
| Dianeal K-141 w/4.25% Dextrose (Travenol) | 42.5 | 132 | 4 | 3.4 | 1.5 | 106 | 35 | | 494 | In 2000 ml. |
| Peritoneal Dialysis w/4.25% Dextrose | 42.5 | 141.5 | | 4.0 | 1.5 | 103 | | 45 | 510 | In 2000 ml. |
| Peritoneal Dialysis Concentrate w/30% D* (American McGaw) | 15 | 130 | | 3.5 | 1.0 | 102 | | 34.5 | 345 | In 2000 ml. |
| Peritoneal Dialysis Concentrate w/50% D* (American McGaw) | 25 | 130 | | 3.5 | 1.0 | 102 | | 34.5 | 395 | In 2000 ml. |
| Peritoneal Dialysis Concentrate w/30% D* Low Sodium (American McGaw) | 15 | 118.5 | | 3.5 | 1.0 | 90.5 | | 34 | 320 | In 2000 ml. |
| Peritoneal Dialysis Concentrate w/50% D* | 25 | 118.5 | | 3.5 | 1.0 | 90.5 | | 34 | 370 | In 2000 ml. |

*Concentration of formulation after dilution with 10 parts water.

In my copending U.S. patent applications filed on even date herewith (identified by U.S. Ser. Nos. 747,292; 747,858; and 748,232) I provide new electrolyte solutions and improved methods for their use which overcome such prior art problems and which not only tend to achieve a normal plasma milliequivalent ratio of sodium cations to chloride anions, but also tend to achieve a normalization of plasma pH and a normalization of the cellular redox state and the cellular phosphorylation potential. Also, these new solutions and methods permit one to avoid usage of the previously employed carboxylic anions, such as acetate, or d,l-lactate alone, which cause adverse effects. The entire teachings and contents of such copending applications I incorporate herein by reference The electrolyte solutions and methods described in such copending application utilize, as above indicated, individual electrolyte concentrations which, in accord with prior art practice, closely resemble (and are in fact intended to closely resemble) the chemical composition of electrolytes in mammalian blood and plasma.

Alternatively it has recently been advocated that the composition of dialysis fluid in the future should resemble that of intercellular fluid (See Parson, F. M. & Stewart, W. K. in *Replacement of Renal Function by Dialysis* (1983) (Drukker, W., Parsons, F. M. & Maher, J. F. eds) pp 148-170, Martin Nijhoff, Hingham).

As will be clear from the disclosures made here, both the view that hemodialysis fluid should mimic plasma or intercellular electrolyte composition is incorrect Rather, hemodialysis fluid electrolyte composition, which will always contact body cells by the media of blood plasma, must contain a precisely calculated degree of deviation from normal in order to achieve electrolyte normality in plasma after blood hemodialysis. The extent and direction of that deviation is determined by the charge and concentration of the non-permeant (Donnan-active) material on the inside (blood side) of the dialysis membrane. In practice, dialysis membranes have pores of average size of 10,000 M. W. The only charged non-permeant material left inside the dialysis cartridge (on the blood side) in a counter-current dialysis are the plasma proteins albumins, globulin and blood cells. As a reasonable approximation, one may take the entire charge as residing on serum albumin because of its very negative isoelectric point. By carefully controlling the pH of the dialysis bath, the clinician may even determine the magnitude of the charge. By then solving a multicomponent, equipressure Donnan equilibrium equation (equation 2 herewith provided) the clinician may then pick precisely the dialysis fluid required by the patient's clinical condition.

In addition to the cause, I have now discovered how to correct the composition of a hemodialysis fluid so that normal concentrations of blood (plasma) inorganic electrolytes can be maintained during hemodialysis. Furthermore, I have discovered a quantitative relationship between hemodialysis so as to produce desired or predictable results. No prior art capability of this sort is believed to have existed.

Apart from the foregoing discoveries, I have further now discovered how to control the rate at which blood (plasma) concentrations materials are changed during a hemodialysis procedure. In the prior art, such rate of change with respect to time has always conformed to a hyperbolic first order rate equation (as hereinbelow explained). In the present invention, method and apparatus are provided which permit one to linearize the rate of change. In addition new compositions are provided which can be regarded as enhancing the utility of such method and apparatus. Nothing in the prior art is believed to suggest such discoveries.

BRIEF SUMMARY OF THE INVENTION

This invention relates to the discovery that the concentrations and distributions of electrolytes in, respectively:
(a) the freshly hemodialyzed blood of a patient, and
(b) the hemodialysis solution used for the hemodialysis of that patient's blood,
are defined by certain mathematical relationships which closely approximate such concentrations and distributions in each of the hemodialyzed blood and the hemodialysis solution.

This discovery permits one to practice various new and very useful processes in the field of hemodialysis. One such process involves preparing an aqueous hemodialysis solution which when used for hemodialysis of a given patient will produce in the blood (plasma) being returned to such patient after hemodialysis thereof a desired or predicted composition of electrolytes.

Another such process relates to estimating (or predicting) the concentration of various blood (plasma) electrolyte components present in the blood being returned to a patient after hemodialysis of such blood with a given aqueous hemodialysis solution.

Another such process involves regulating the anionic charge associated with a patient's own polyanionic blood proteins of predetermined and variable charge (especially albumin) for purposes of filling the anion gap, normalizing the Na:Cl milliequivalent ratio, or the like.

Other such processes will be apparent to those skilled in the art from the teachings of the present specification and claims. This discovery additionally permits one to prepare new and useful aqueous electrolyte solutions.

When used as hemodialysis solutions, the solutions of this invention use polyanions of predetermined and variable charge present in a patient's own blood (especially albumin) to fill the anion gap and to normalize the Na:Cl milliequivalent ratio in the patient's own blood (plasma).

Another feature of the present invention is that hemodialysis solutions of the present invention are provided which have abnormal respective concentrations of electrolytes whereas previous fluids attempted to mimic plasma concentrations of electrolytes. Yet when such solutions are used for hemodialysis, they tend to result inherently in normalization of the concentrations and distributions of electrolytes in the blood (plasma) of a patient hemodialyzed therewith. In other words, in order to achieve normality in concentration and distribution of electrolytes in blood (plasma), one employs hemodialysis solutions of the present invention wherein abnormal, relative to normal blood (plasma), concentrations of electrolytes are incorporated in a rationally predictable manner.

In another feature of the present invention, a patient's own albumin is employed to normalize the Na:Cl milliequivalent ratio present in that patient's blood.

Optionally, one can incorporate into composition and processes of the present invention additional features. For example, one can utilize in the practice of this invention aqueous solutions for hemodialysis wherein:
(a) the ratio of sodium cation milliequivalents per liter to the chloride anion milliequivalents per liter within the range found in normal mammalian blood plasma without inducing the profound metabolic pathology produced by the current fluids which utilize lactate, acetate, or other unsafe anionic metabolites, and (b) there is a physiologically effective amount of at least one near equilibrium couple selected from the group consisting of:
  (1) bicarbonate⁻ and carbon dioxide,
  (2) l-lactate⁻ and pyruvate⁻ and
  (3) d-betahydroxybutyrate⁻ and acetoacetate⁻.

Also, preferably, such solutions have a pH in the range from 5 to 9.

Thus, the advantages and utilities associated with, for example, the compositions described in my above identified copending U.S. patent application can be achieved in the practice of my present invention, but, in addition, by taking into consideration the hereindescribed mathematical relationships existing between hemodialysis solution and blood being, or to be, dialyzed therewith, regulation of blood and hemodialysis solution (as desired) inorganic electrolyte concentrations is achievable as is regulation of a patient's own polyanionic blood protein charge. The present invention provides compositions and methods for correcting the anion gap, and such processes and compositions and methods take into account the special Donnan forces operating during hemodialysis.

The present invention makes possible the preparation of electrolyte solutions for various special purposes, such as in situations where a patient is to be hemodialyzed to achieve changes in blood composition not associated with or caused by renal failure, as herein described and exemplified, including acidosis, poisoning, hyperkalemia, and the like.

The present invention provides techniques for achieving solutions from the mathematical formulae described below showing the relationship between the electrolytes and non-permeant charged material on patient's blood and the charged electrolytes in a hemodialysis fluid to be or being used to hemodialyze that blood.

These mathematical relationships can be used for regulating the relationship between other fluids besides hemodialysis fluids and blood. Thus, for example, the present invention provides a general process for estimating the concentration of electrolytes in a solution containing at least one non-permeant ionically charged material after such solution has been dialyzed through an inert membrane structure, and, conversely, the present invention provides a general process for estimating the concentration of electrolytes needed in a starting solution which is to be used to dialyze a solution containing at least one non-permeant ionically charged material in order to achieve a desired or predetermined electrolyte composition in the latter solution. Examples of practical applications include preparing dried plasma protein in an electrolyte solution ready for I.V. infusion, and the like.

This invention further relates to the discovery that, in a dialysis, one can control the rate of change in concentration of a diffusible material in a fluid on one side of an inert dialysis membrane relative to another fluid on the opposing side of such membrane. The rate is preferably, in accord with this invention, linearized, but may be made to be hyperbolic or any other mathematically definite shape.

In the prior art, where the respective fluids on each side of this membrane were initially of a fixed composition, the rate of change conformed always to a first order rate equation wherein characteristically the time $t_{\frac{1}{2}}$ required to achieve a concentration change from an initial concentration $C_o$ and a final concentration $C_F$ is very much less than one half the total time $t_f$ required to achieve a concentration value approaching $C_F$. By the present invention, the rate of change in any dialyzable component may be regulated by changing the concentration of that component over time in the dialysis fluid. Control of the rate of change, allows the physician to either decrease the morbidity induced by a rapid initial change characteristic of present dialysis (1st order rate) or to shortened the length of time required for dialysis in those patients, able to tolerate rapid changes.

The control of rate of change of concentration in accord with the teachings of the present invention makes possible many new and improved dialysis techniques where a given dialysis procedure can be varied to meet a physician determined optimized dialysis rate and time for a given patient, thereby to maximize benefits to that patient.

This discovery thus provides processes for regulating the concentrations and distribution of electrolytes in living animal cells which are being treated (contacted) with an electrolyte containing fluid by systematically changing (altering) the electrolyte composition of such fluid over a predetermined (selected) interval of time. The rate of change, that is, the slope and the shape of the curve of rate of change versus time elapsed, is variable, but the final fluid composition and the starting fluid composition can be regarded as predeterminable.

The present processes make possible the achievement of electrolyte compositional changes in extra cellular fluids which cannot be achieved by the conventional method of merely admixing (or exposing) a particular extracellular fluid to an electrolyte composition of fixed (predetermined) electrolyte components as respects type and weight. Such conventional method results in a fixed and predictable rate of change with respect to time that is fully defined by a simple first order (hyperbolic) rate equation.

The invention further provides an embodiment of apparatus for practicing such methods wherein a plurality of separately stored master components or batches (or equivalent) of pre-chosen starting materials are automatically blended together in a prechosen sequence and/or at prechosen rate(s) so as to produce product electrolyte compositions that is continuously (or discontinuously, if desired) systematically varied as to component concentration and/or component selection.

The invention further relates to compositions and fluids useful in the practice of such processes and in the operation of such apparatus.

The present invention can be used for various applications, such as, for examples:

(1) in human dialysis (especially hemodialysis) to control the rate of electrolyte change in a patient's blood,
(2) in preparing intravenous human electrolyte fluid for administration to a patient,
(3) for preparation of blood or blood fractions for administration to a patient,
(4) for preparation of nutrients to be administered, and
(5) to patients or to living cells, and the like.

An optional fixture of the present invention is that one can, by the practice of this invention, regulate the electrolyte composition properties of human blood or plasma in a living patient by changing in a predetermined systematic manner over a predetermined interval of time one or more of such blood electrolyte compositional variables or characteristics such as:

(1) polyanionic protein charge on blood being dialyzed.
(2) concentration of one or more major blood cations and/or anions.
(3) concentration of diffusible non-ionics and the like.

Another optional feature of the present invention is that one can avoid the use of acetate anions in a dialysis fluid or in a parenteral fluid (including intravenous fluids) because use of acetate or d,l lactate ions alone as is conventionally practiced in the art has definable pathological consequences.

Another optional feature of the present invention is that one can incorporate bicarbonate/$CO_2$ into an electrolyte solution in variable quantities.

Another optional feature of the present invention is that one can use cell permeant near-equilibrium couples in an electrolyte solution (so as to regulate intracellular redox and phosphorylation states), Another feature of this invention is that one may regulate the charge on a non-permeant polyionic substance by regulation of pH, metal content and concentration of other effectors of charge.

The specified milliequivalent ratio of sodium to chloride in normal mammalian blood generally is believed to be in the range from about 1.24:1 to 1.47:1. In the case of a normal human adult, this range is now believed to extend (based on published information) from about 1.24:1 to 1.45:1 and preferably from about 1.33:1 to 1.42:1 and most preferably from about 1.36:1 to 1.42:1. These ratios of Na:Cl are typically employed in solutions used in the practices of this invention. Ratios above 1.47, i.e. from about 1.47 to about 1.6 can be used within the spirit and scope of this invention as when it is the physician's conscience intention to create an abnormal Na:Cl ratio as, for example, to create an excess of alkali reserve; however, such higher ratios are generally not presently preferred for general usage. In the case of dialysis fluids or to create an alkalotic condition in a cell or to correct an existent acidosis, this Na:Cl ratio can range to 1.55.

The total quantity, or sum (sigma), of bicarbonate anions and carbon dioxide present in a solution of this invention ranges from 0 to about 55 millimoles per liter of solution. The ratio of bicarbonate milliequivalents per liter to dissolved carbon dioxide milliequivalents per liter in a solution of this invention can range from about 1:1 to 55:0.1 and preferably 11:1 to 24:1. More preferably, such total ranges from about 10 to 45 mM/l and such ratio ranges from about 18.1 to 26:1, and still more preferably such total ranges from about 23 to 35 mM/l while such ratio ranges from about 19:1 to 21:1. A ratio of 19.95 for [$HCO_3^-$]/[$CO_2$] gives a pH of 7.4 which is presently particularly preferred.

The total quantity, or sum (sigma) of l-lactate anions and pyruvate anions present in a solution of this invention ranges from 0 to about 55 millimoles per liter of solution. The ratio of L-lactate anion milliequivalents per liter to pyruvate anion milliequivalents per liter in a solution of this invention can range from about 20:1 to 1:1. Preferably, such total quantity ranges from about 0.5 to 10 mM/l and such ratio ranges from about 3:1 to 15:1, and more preferably such total quantity ranges from about 2 to 8 mM/l while such ratio ranges from about 5:1 to 12:1.

The total quantity, or sum (sigma) of d-betahydroxybutyrate anions and acetoacetate anions present in a solution of this invention ranges from about 0 to about 55 millimoles per liter of solution. The ratio of d-betahydroxybutyrate anion milliequivalents per liter to acetoacetate milliequivalents per liter in a solution of this invention can range from about 6:1 to 0.5:1. Preferably, such total ranges from about 1 to 10 mM/l and such ratio ranges from about 4:1 to 1:1, and more preferably such total ranges from about 2 to 5 mM/l while such ratio ranges from about 3:1 to 1.5:1.

By the term "milliequivalent ratio" as sometimes used herein, reference is had the ratio of milliequivalents per liter of one substance to milliequivalents per liter of another substance in a aqueous medium.

One of the three near equilibrium couples employed in the practice of this invention (the bicarbonate$^-$/carbon dioxide couple) tends, as used in this invention, to regulate the concentration of hydrogen ions in blood (plasma) and in the treated mammal's cells, and each one of such couples tends to normalize the redox state of each of the three pyridine nucleotide couples. The phosphorylation potential also tends to be normalized. Also, each such near equilibrium couple when used as herein described constitutes a safe entry point into the metabolic system of a mammal.

By the term "safe entry point" as used herein reference is generally had to a metabolite which, in living tissue or cells:

(1) does not cause a massive buildup of one or more of intermediate cellular metabolites,
(2) does not cause a severe disruption of any one of the controlling nucleotide ratios in a living cell
(3) can be added to a physiological system of a living mammal at a concentration level which is greater than that which is found normally in such system (such as blood plasma of a fasting mammal) without causing any appreciable distortion in metabolism and without causing any pathological conditions to arise, and
(4) may be found in normal variants of the physiological state as when the total of D-betahydroxybutyrate plus acetoacetate reaches a level of about 6 to 8 mM/L in three day fasting man, or the total of l-lactate plus pyruvate rises to a level of about 5 to 6 mM/l in a jogging normal man.

Further, each such above described near equilibrium couple in this invention exhibits a distribution or permeability between intracellular fluid and extracellular fluid such that the ratio of the concentrations in, respectively, intracellular fluid to extracellular fluid ranges from about 1.0:1 to 1.5:1 in most all mammalian cells.

Osmotically active substances (preferably non ionic) incorporated with the solutions of this invention preferably should each constitute a safe entry point. For example, glucose above 13 mM/l is higher than ever occurs under normal physiological conditions in a healthy man. Use of glucose above 13 mM/l (as in the widely used 5% glucose solution) as a calorie source is, apart from consideration of the source of pathology, and apart from the carboxylate couples considered herein to be an acceptable source of calories. The extreme ability of the mammalian body to regulate its glucose metabolism makes it far to be preferred over other possible nonionics, such as fructose or glycerol, which enter the metabolic system in an uncontrolled manner causing pathologic changes such as are already referenced, and so such are not safe entry points.

Characteristically, a solution used in the practice of this invention contains from about 120 to 165 millimoles per liter of sodium cations, and more preferably from about 129 to 163.5 mM/l and most preferably from about 136 to 145 mM/l. In addition, a solution contains sufficient chloride anions to produce a milliequivalent ratio of sodium cations to chloride anions in the range above defined.

Optionally, in addition to sodium, a solution of this invention can contain one or more of the following additional metallic cations each in a respective quantity as below indicated:

| cation component | Quantity range (millimoles per liter) | |
| --- | --- | --- |
| | broad | preferred |
| potassium | 0–40 | 0–5 |
| calcium | 0–10 | 0–1.5 |
| magnesium | 0–10 | 0–1 |

Optionally a solution of this invention can have additionally incorporated (dissolved) therein from 0 to about 855 millimoles per liter of at least one substantially nonionic (including zwitterionic) osmotically active substance (which is preferably metabolizable).

A solution used in the practice of this invention is further characterized by generally having
  (1) sufficient total substances dissolved therein to produce and osmolarity ranging from about 260 to 850 milliosmoles (mOs), and preferably from about 265 to 550 mOs, and most preferably from about 280 to 320 in mOs;
  (2) the relationship between total (dissolved) ionic substances is such that the pH ranges from about 5 to 9, and preferably from about 6.9 to 8.6; and most preferably from about 7.35 to 7.55;
  (3) the charges of all cations equal the charges of all anions; and
  (4) the minimum total concentration of all such near equilibrium couple(s) present is at least about 0.1 millimoles per liter, and preferably is at least about 0.5 mM/l, and more preferably about 2 mM/l, while the maximum concentration thereof is preferably not more than about 80 and more preferably is not more than about 61 mM/l and most preferably is not more than about 50 mM/l.

Examples of usable such nonionic substances include glucose, glycerol, fructose, sorbitol, and the like. Glucose is presently most preferred.

As hereinbelow explained, the processes and the solutions of the present invention find use in a wide variety of therapeutic applications, such as in electrolyte and fluid replacement, parenteral nutrition, and dialysis.

Various additional objects, aims, purposes, features, advantages, applications, variations, and the like will be apparent to those skilled in the art from the teachings of the present specification taken with the claims.

BRIEF DESCRIPTION OF DRAWINGS

In the drawings.

FIG. 7 is a diagrammatic illustration of one embodiment of a hemodialysis apparatus wherein dialysis fluid composition can be varied, either batchwise from one patient to another, or continuously during the dialysis of a given patient to achieve a desired rate of change in the patient's blood electrolyte concentration or both if desired.

DETAILED DESCRIPTION

Figure 1A:
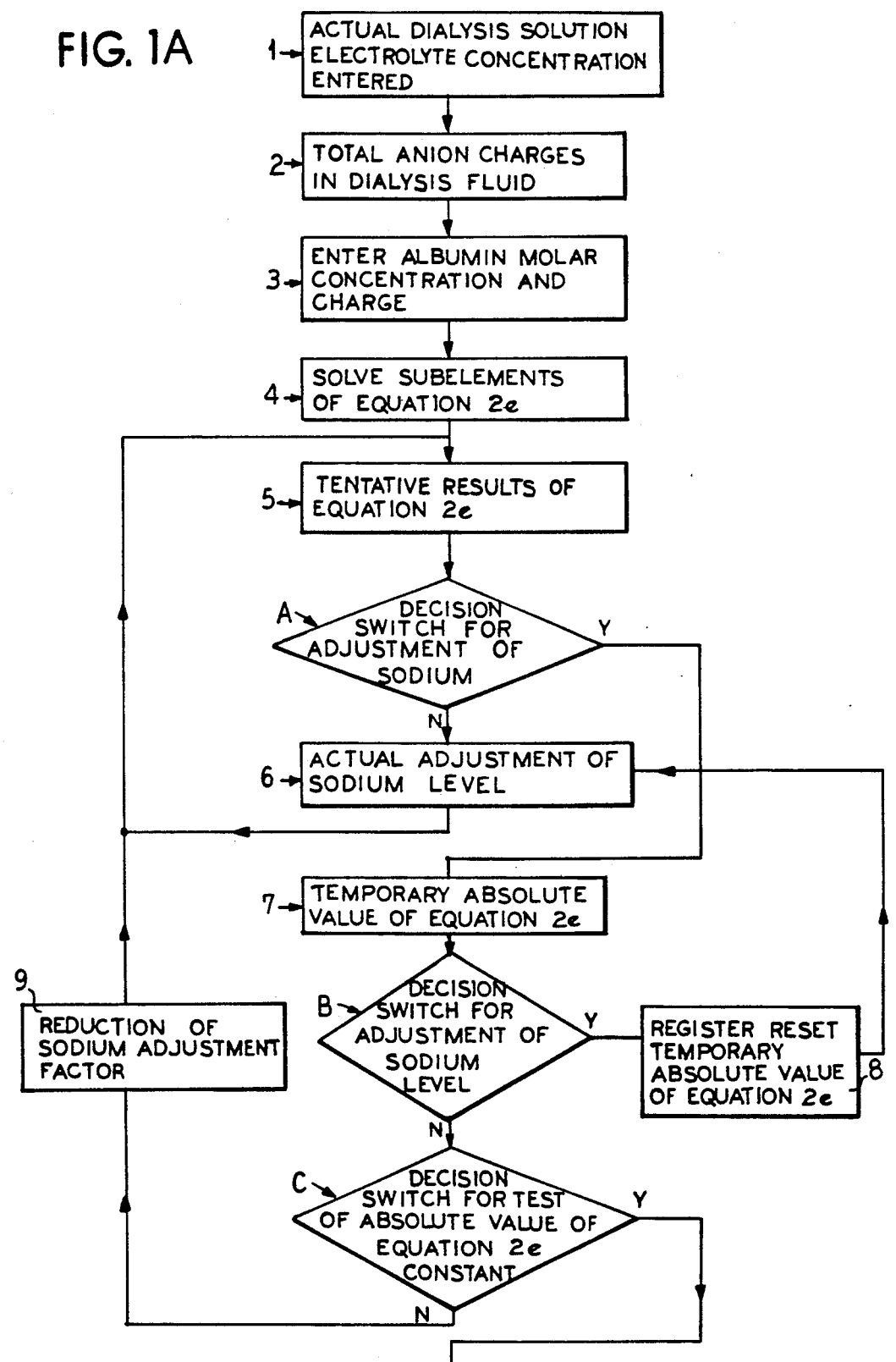
FIG. 1 (sheets A, B, C, and D) is a flow chart of one embodiment of a computer program for solving in a hemodialysis application the multicomponent interrelationships involved in the distribution of charged ions in a multicomponent Donnan equilibrium situation involving a permeant membrane the present program being capable of identifying the plasma composition which will be achieved in a given patient who is to be hemodialyzed with a particular, predetermined hemodialysis fluid composition.

As indicated above, a mathematical interrelationship between a first fluid containing a non-permeant charged material and another fluid disposed on an opposed side of a semi-permeable membrane relative to the side of such membrane on which is disposed said first fluid is now believed to exist, and this relationship is represented by the following set of equations:

O. Eqn 0 —The Second Law

J. Willard Gibbs. On the equilibrium of heterogeneous substances. *J Conn Acad Sci* 1876; III : 343.

0-1 Definition of Gibbs Free Energy and Other Properties of State:
$$G = H - TS$$
where:
$G \sim$ Gibbs free energy
$H \sim$ Enthalpy or heat content
$T \sim$ absolute temperature
$S \sim$ Entropy, or state of randomness or disorder 0-1a Entropy may be more rigorously defined by statistical and quantum mechanics in the Boltzmann Equation:
$$S = k_B \ln \Omega$$
where:
$S \sim$ Entropy -continued $k_B \sim$ Boltzmann constant $= \dfrac{R \text{ (gas constant)}}{\text{Avagadro's number}}$ $= 1.38 \times 10^{-23} J/°K.$ $\Omega \sim$ Degeneracy 0-2 $\Delta G = \Delta H - T \Delta S$
where $\Delta \sim$ change in 0-3 Standard Free Energy $\sim \Delta G°$ $\Delta G = \Delta G° + RT \ln \dfrac{[\text{products}]}{[\text{reactants}]}$ where:

$R \sim$ gas constant
$= 1.987$ calories/°K./mole
and °K. $\sim 273 + $°C.
$T = $ °K.
$\ln \sim 2.303 \log_{10}$ 0-3a $\Delta G° = -RT \ln K_{eq}$
where:

$K_{eq} \sim \dfrac{[\text{products}]}{[\text{reactants}]}$ 0-4 At equilibrium, $\Delta G = 0$, so in $A + B \rightleftharpoons C + D$ $\Delta G = -RT \ln K_{eq} + RT \ln \dfrac{[C][D]}{[A][B]}$ where:
[ ] $\sim$ activity or $\sim$ concentration I Eqn 1 —The Henderson-Hasselbalch Equation The major buffer and controller of extra- and intracellular pH.

Henderson LH. Blood, A Study in General Physiology. *Silliman Lectures*, Yale University Press, 1928

1.a $pH = pK_{a'} + \log \dfrac{[HCO_3^-]}{[CO_2]}$ where:
$pK_{a'} = 6.10$ at 38° C. and serum concentrations of electrolytes 1.b The solubility of $CO_2$ in fluid, i.e. dissolved $CO_2$ gas plus $H_2CO_3$ from:

$CO_2 + H_2O \rightleftharpoons H_2CO_3$ $[CO_2]$ in mmol/liter $= \dfrac{pCO_2 \text{ in mmHg}}{760 \text{ mmHg}} \cdot$

$\dfrac{a \text{ ml } CO_2/\text{ml of } H_2O}{22.26 \text{ L/mole}} \cdot \dfrac{1000 \text{ mmol}}{\text{mole}}$ $a_{CO_2} = 0.553$ ml $CO_2$/ml serum $H_2O$ at 38° C. from:
Van Slyke DD. J Biol Chem 73: 765-799, 1928.

1.c The pH of a bicarbonate containing solution to which has been added a carbocylic acid such as acetic, lactic, acetoacetic acid with a $pK'$ in the 3 to 4 range and where the concentration of $HCO_3^-$ is much larger that the concentration of carboxcylic acid:

$pH = pK_{a'} - \log \left\{ \dfrac{[HCO_3^-]}{2([HCO_3^-] - [HA])} - \dfrac{1}{2} \right\}$ Thus adding 1.8 nM Hlactate and 0.2 mM Hpyruvate to 25 mM $NaHCO_3$ yields what pH?

-continued $pH = pK_{a'} - \log \left\{ \dfrac{[25]}{2([HCO_3 - [HA])} - \dfrac{1}{2} \right\}$ $= 6.1 - (1.36)$ $= 7.46$ II Donnan Equilibrium Equation Donnan FG. *Z Electrochem* 17: 572, 1911
Donnan FG. *Chem Rev* 1: 73-90, 1924.

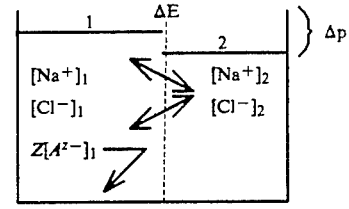

[ ] $\simeq$ activity $\simeq$ concentration
$A \simeq$ non-diffusable polyanion
$Z \simeq$ valance of polyanion 1. From Gibbs (Eqn 0)

$RT \ln \dfrac{[Cl^-]_1}{[Cl^-]_2} + RT \ln \dfrac{[Na^+]_1}{[Na^+]_2} = 0$

Or:

1.a $\dfrac{[Cl^-]_1}{[Cl^-]_2} = \dfrac{[Na^+]_2}{[Na^+]_1}$

Therefore: $\dfrac{[Cl^-]_1}{[Cl^-]_2} = \dfrac{[Cl^-]_2}{[Cl^-]_1 + Z[A^{z-}]_1} = \dfrac{[Na^+]_2}{[Na^+]_1}$ and for polyvalents:

$\left( \dfrac{[\text{Anions}]_1}{[\text{Anions}]_2} \right)^{1/z \text{ anions}} = \left( \dfrac{[\text{Cations}]_2}{[\text{Cations}]_1} \right)^{1/z \text{ cations}}$ 2. From the Law of Electrically Neutrality:
$[Na^+]_2 = [Cl^-]_2$
$[Na^+]_1 = [Cl^-]_1 + Z[A^{z-}]_1$ 3. Quadratic equation:

$x = \dfrac{-b + \sqrt{b^2 - 4ac}}{2a}$

EXAMPLE

Consider albumin dialyzed against 100% $CO_2/3.13$ $NaHCO_3$ buffer with 1.17 mM albumin (i.e. 8% solution). Hypothetically keep charge on albumin at $-20$/mole.

$\dfrac{[HCO_3^-]_i}{[HCO_3^-]_o} = \dfrac{[HCO_3^-]_o}{[HCO_3^-]_i + 20[Alb^{-20}]} = \dfrac{[Na^+]_o}{[Na^+]_i}$ $\dfrac{[HCO_3^-]_i}{[3.13 \times 10^{-3}]} = \dfrac{[3.13 \times 10^{-3}]}{[HCO_3^-]_i + 20[1.17 \times 10^{-3}]}$ $[HCO_3^-]_i = 0.4 \times 10^{-3} M$

II Eqn 2 Multicomponent Donnan Equilibrium System for Solutions Such as the Heaodialysis of Blood Plasma Electrolytes where $\Delta p = 0$ and all components but albumin are permeant. Subscript$_o$ ~ in dialysis fluid, subscript$_i$ ~ in patient's plasma, $\Delta p$ ~ difference in pressure.

2.a. $\quad \dfrac{[Na^+]_i}{[Na^+]_o} = \dfrac{[K^+]_i}{[K^+]_o} = \left(\dfrac{[Ca^{2+}]_i}{[Ca^{2+}]_o}\right)^{\frac{1}{2}} = \left(\dfrac{[Mg^{2+}]_i}{[Mg^{2+}]_o}\right)^{\frac{1}{2}} =$ $\dfrac{[Cl^-]_o}{[Cl^-]_i} = \dfrac{[HCO_3^-]_o}{[HCO_3^-]_i} = \left(\dfrac{[\Sigma Pi]_o}{[\Sigma Pi]_i}\right)^{1/1.8} = \dfrac{[lac^-]_o}{[lac^-]_i} =$ $\dfrac{[pyr^-]_o}{[pyr^-]_i} = \dfrac{[acac^-]_o}{[acac^-]_i} = \dfrac{[BHB^-]_o}{[BHB^-]_i} = \dfrac{[acet^-]_o}{[acet^-]_i}$ Statement of electrical neutrality on two sides of an uncharged membrane 2.b.1. $[Na^+]_o + [K^+]_o + 2[Ca^{2+}]_o + 2[Mg^{2+}]_o = [Cl^-]_o +$ $[HCO_3^-]_o + 1.8[\Sigma Pi^{-1.8}]_o + [lac^-]_o + [pyr^-]_o + [acac^-]_o +$ $[BHB^-]_o + [acet^-]_o$ 2.b.2. $[Na^+]_i + [K^+]_i + 2[Ca^{2+}]_i + 2[Mg^{2+}]_i = [Cl^-]_i +$ $[HCO_3^-]_i + 1.8[\Sigma Pi^{-1.8}]_i + [lac^-]_i + [pyr^-]_i + [acac^-]_i +$ $[BHB^-]_i + [acet^-]_i + Z[prot^{z-}]_i$ Distribution of cations on two sides of the membrane:

2.c $\quad [K^+]_i = [K^+]_o \dfrac{[Na^+]_i}{[Na^+]_o}; \; [Ca^{2+}]_i = [Ca^{2+}]_o \left(\dfrac{[Na^+]_i}{[Na^+]_o}\right)^2;$ $[Mg^{2+}]_i = [Mg^{2+}]_o \left(\dfrac{[Na^+]_i}{[Na^+]_o}\right)^2$ Distribution of Anions:

2.d $\quad [Cl^-]_i = \dfrac{[Na^+]_o}{[Na^+]_i}[Cl^-]_o; \; [HCO_3^-]_i = \dfrac{[Na^+]_o}{[Na^+]_i}[HCO_3^-]_o;$ $[acet^-]_i = \dfrac{[Na^+]_o}{[Na^+]_i}[acet^-]_o; \; [\Sigma Pi]_i = \left(\dfrac{[Na^+]_o}{[Na^+]_i}\right)^{1.8}[\Sigma Pi]_o;$ $[lac^-]_i = \dfrac{[Na^+]_o}{[Na^+]_i}[lac^-]_o; \; [pyr^-]_i = \dfrac{[Na^+]_o}{[Na^+]_i}[pyr^-]_o;$ $[acac^-]_i = \dfrac{[Na^+]_o}{[Na^+]_i}[acac^-]_o; \; [BHB^-]_i = \dfrac{[Na^+]_o}{[Na^+]_i}[BHB^-]_o$ Now solving for $[Na^+]_i/[Na^+]_o$ for a dialysis fluid$_o$ of known composition:

2.e $\quad \dfrac{[Na^+]_i}{[Na^+]_o}\left\{[Na^+]_o + [K^+]_o + 2\dfrac{[Na^+]_i}{[Na^+]_o}([Ca^{2+}]_o +\right.$ $\left.[Mg^{2+}]_o)\right\} = \dfrac{[Na^+]_o}{[Na^+]_i}\left\{[Cl^-]_o + [HCO_3^-]_o + [acet^-]_o +\right.$ $[lact^-]_o + [pyr^-]_o + [acac^-]_o +$ $\left.[BHB^-]_o + 1.8\left(\dfrac{[Na^+]_o}{[Na^+]_i}\right)^{0.8}[\Sigma Pi]_o + \dfrac{[Na^+]_i}{[Na^+]_o}|Z|[prot^{z-}]\right\}$ and:

2.f $\quad \dfrac{[Na^+]_o + [K^+]_o}{[Na^+]_o^2}[Na^+]_i^2 +$ $\dfrac{2([Ca^{2+}]_o + [Mg^{2+}]_o)}{[Na^+]_o^3}[Na^+]_i^3 - |Z|\dfrac{[prot^{z-}]}{[Na^+]_o}[Na^+]_i -$ $(1.8[\Sigma Pi]_o[Na^+]_o^{0.8})[Na^+]_i^{(-0.8)} = [Cl^-]_o + [HCO_3^-]_o +$ $[acet^-]_o + [lact^-]_o + [pyr^-]_o + [acac^-]_o + [BHB^-]_o$ Plasma [concentration] ~ 0.935 × plasma H$_2$O [concentration]

III Eqn 3. Nernst Equation —$\Delta E$

Nernst W. *Theoretical Chemistry*, 4th Edition, 1904, McMillan, London. See also *Silliman Lecture*, 1906, Yale U. Press, New Haven.

3. $\quad \Delta E = -\dfrac{RT}{nF} \ln \dfrac{[anion^-]outside}{[anion^-]inside}$ or:

$\Delta E = -\dfrac{RT}{nF} \ln \dfrac{[cation^+]inside}{[cation^+]outside}$ where:
at 38° C. T ~ 311° K
R, the gas constant, ~8.314 joules/degree/mole
n ~ number of equivalents
F, the Faraday, ~96,494 coulombs
$\Delta E$ ~ potential in volts
To convert ln to log$_{10}$, multiply be 2.303

From Cornell N, *Anal Biochem* 1980: 102: 326–331, for isolated hepatocytes from starved rats incubated in Krebs-Henseleit:

$\Delta E = -0.0617 \log \dfrac{[0.128 \text{ M Cl}^-]outside}{[0.041 \text{ M Cl}^-]inside}$ $\Delta E = -0.0305$ V or $-30.5$ mV and for cat brain, from Eccles, JC. *The Physiology of Nerve Cell*, 1957, Johns Hopkins U Press, Baltimore.

$\Delta E = -0.0617 \log \dfrac{[0.125 \text{ M Cl}^-]outside}{[0.009 \text{ M Cl}^-]inside}$ $\Delta E = -0.0705$ V or $-70.5$ mV

3. b Redox Potential of Half Reactions $E_h = E° + \dfrac{RT}{nF} \ln \dfrac{[oxidized]}{[reduced]}$ where:
R ~ 8.31431 J/° K/mole
T ~ ° K
n ~ number of electrons
F ~ Faraday ~ 96,494 coulombs
ln ~ 2.303 log$_{10}$

IV Eqn 4 Redox Sate Equations. $[NAD^+]/[NADH]$ or $[NADP^+]/[NADPH]$.

Near equilibrium reactions are given a number depending upon location. The $E^o$ of the $[NAD^+]/[NADH]$ couple at pH 7 is $-0.32$ V. That of the $[NADP^+]/[NADPH]$ couple, $-0.335$ V.

| Abbreviation Enzyme No. | Definition of $K_{eq}$ | Value of $K_{eq}$ at pH = 0 | Value of $K_{eq}$ at pH 7 | $E^{o'}$ at pH 7.0 oxidized/reduced V | $E^{o'}$ at pH 7.0 $CO_2 = 1.5$ mM or 0.5 mM $NH_4^+$ or 1 mM Pi V | |
|---|---|---|---|---|---|---|
| | Cytoplasmic NAD - Linked Dehydrogenases | | | | | |
| 4c1 | $K_{LDH} = \frac{[pyruvate^-][NADH][H^+]}{[l\text{-}lactate-][NAD+]}$ EC 1.1.1.27 | $1.11 \times 10^{-11}$ M | $1.11 \times 10^{-4}$ | $-0.201$ | | |
| 4c2 | $K_{MDH} = \frac{[oxaloacetate^{2-}][NADH][H^+]}{[l\text{-}malate2-][NAD+]}$ EC 1.1.1.37 | $2.86 \times 10^{-12}$ M | $2.86 \times 10^{-5}$ | $-0.184$ | | |
| 4c3 | $K_{GPDH} = \frac{[\alpha\text{-}glycerol\text{-}P^{2-}][NADH][H^+]}{[DHAP2-][NAD+]}$ EC 1.1.1.94 | $1.3 \times 10^{-11}$ M | $1.3 \times 10^{-4}$ | $-0.203$ | | |
| 4c4 | $K_{GAPDH} = \frac{[1,3\ DiPG^{4-}][NADH][H^+]}{[GAP2-][Pi2-][NAD+]}$ EC 1.2.1.12 | $5.3 \times 10^{-8}$ M | $5.3 \times 10^{-1}$ | $-0.302$ | $-0.222$ | Here, Pi is a reactant |
| | $K_{ADH} = \frac{[acetaldehyde][NADH][H^+]}{[ethanol][NAD+]}$ EC 1.1.1.1 | $1.94 \times 10^{-11}$ M | $1.9 \times 10^{-4}$ | $-0.209$ | | |
| | $K_{ldDH} = \frac{[d\text{-}fructose][NADH][H^+]}{[d\text{-}sorbitol][NAD+]}$ EC 1.1.1.14 | $1.14 \times 10^{-9}$ M | $1.14 \times 10^{-2}$ | $-0.262$ | | |
| | Mitochondrial NAD - Linked Dehydrogenases | | | | | |
| 4m1 | $K_{HBDH} = \frac{[acetoacetate^-][NADH][H^+]}{[d\text{-}B\text{-}hydroxybutyrate-][NAD+]}$ EC 1.1.1.30 | $4.93 \times 10^{-9}$ M | $4.93 \times 10^{-2}$ | $-0.281$ | | |
| 4m2 | $K_{GlDH} = \frac{[\alpha\text{-}KG^{2-}][NH_4^+][NADH][H^+]}{[l\text{-}glutamate][NAD+]}$ EC 1.4.1.3 | $3.87 \times 10^{-13}$ $M^2$ | $3.87 \times 10^{-6}$ M | $-0.158$ | $-0.257$ | |
| | $K_{AlDH} = \frac{[acetate^-][NADH][H^+]^2}{[acetaldehyde][NAD+]}$ EC 1.2.1.3 | $1.45 \times 10^{-5}$ $M^2$ | $1.45 \times 10^{+9}$ | $-0.596$ | | |
| | Cytoplasmic NADP - Linked Dehydrogenases | | | | | |
| 4T1 | $K_{IcDH} = \frac{[\alpha\text{-}KG^{2-}][CO2][NADPH]}{[l_s\text{-}isocitrate3-][NADP+]}$ EC 1.1.1.42 | 1.17 M | 1.17 M | $-0.337$ | $-0.422$ | Here, $CO_2$ is a reactant |
| 4T2 | $K_{Malic\ Enz} = \frac{[pyruvate^-][CO2][NADPH]}{[malate2-][NADP+]}$ EC 1.1.1.40 | $3.44 \times 10^{-2}$ M | | | | |
| 4T3 | $K_{6PGDH} = \frac{[ribulose\ 5\text{-}P^{2-}][CO2][NADPH]}{[6\text{-}phosphogluconate3-][NADP+]}$ EC 1.1.1.43 | $1.72 \times 10^{-1}$ M | | | | |
| | Linking Isomerases | | | | | |
| 4L1 | $K_{GOT} = \frac{[\alpha\text{-}KG^{2-}][l\text{-}aspartate^-]}{[l\text{-}glutamate-][oxaloacetate-]}$ EC 2.6.1.1 | 6.61 | | | | |
| 4L2 | $K_{GPT} = \frac{[\alpha\text{-}KG^{2-}][l\text{-}alanine]}{[l\text{-}glutamate-][pyruvate-]}$ EC 2.6.1.2 | 1.52 | | | | |
| 4L3 | $K_{TPI} = \frac{[dihydroxyacetone\text{-}P^{2-}]}{[glyceraldehyde\ 3\text{-}P2-]}$ EC 5.3.1.1 | 22 | | | | |

*See ref.

References for Values of Near-Equilibrium Reactions in Equation 4

| Equation | Abbreviation | Reference |
|---|---|---|
| 4C1 | $K_{LDH}$ | Williamson DH, Lund P, Krebs HA. Biochem J 103: 514-527, 1967 |
| 4C2 | $K_{MDH}$ | Guynn R, Gelberg H, Veech RL. J Biol Chem 248: 6957-6965, 1973 |
| 4C3 | $K_{GPDH}$ | Russman W. Thesis, Munich, 1969. |
| 4C4 | $K_{GAPDH}$ | Cornell N, Leadbetter M, Veech RL. J Biol Chem 254: 6522-6527, 1979 |
| 4M1 | $K_{HBDH}$ | Williamson DH, Lund P, Krebs HA. Biochem J 103: 514-527, 1967 |
| 4M2 | $K_{GLDH}$ | Engel P, Dalziel K. Biochem J 105: 691-695, 1967 |
| 4T1 | $K_{IcDH}$ | Londesbourgh J, Dalziel K. Biochem J 110: 217-222, 1968 |
| 4T2 | $K_{M.E.}$ | Veech R, Eggleston LV, Krebs HA. Biochem J 115: 609-619, 1967 |
| 4T3 | $K_{6PGDH}$ | Villet R, Dalziel K. Biochem J 115: 633-638, 1969 |
| 4L1 | $K_{GOT}$ | Krebs HA. Adv Enz Reg 13: 449-472, 1975 |
| 4L2 | $K_{GPT}$ | Krebs HA. Adv Enz Reg 13: 449-472, 1975 |
| 4L3 | $K_{TPI}$ | Veech RL, Raijman L, Dalziel K, Krebs HA. Biochem J 115: 837-842, 1969 |

*The enzyme aldose reductase EC 1.1.1.21 may be redox active during fructose infusion in certain tissues.
The reaction is:

$$K_{Aldose\ R} = \frac{[d\text{-sorbital}][NADPH][H^+]}{[d\text{-glucose}][NADP^+]} \cdot 2 \times 10^{-11} M.* \text{ My estimate}$$

For description, see Hayman S, Kinoshita JH. J Biol Chem 240: 877, 1965

V Eqn 5 Phosphorylation State Equations —[ΣATP]/[ΣADP][ΣPi]

Veech RL, Lawson, JR, Cornell NW, Krebs HA. *J Biol Chem* 254: 6538-6547, 1979

5a. The equilibrium constant of the glyceraldehyde 3-phosphate dehydrogenase (EC 1.1.1.29) and 3 phosphoglycerate kinase reactions (EC 2.7.2.3) at 38° C., I = 0.25, and free [Mg$^{2+}$] = 1 mM is:

$$K_{G+G} = \frac{[\Sigma 3PG]}{[\Sigma GAP]} \cdot \frac{[\Sigma ATP]}{[\Sigma ADP][\Sigma Pi]} \cdot \frac{[NADH][H^+]}{[NAD+]} = 1.83 \times 10^{-4}$$

5b. Combining the above reaction with $K_{LDH}$ and substituting [DHAP] = [GAP]/22

$$\frac{K_{G+G}}{K_{LDH}} = \frac{[\Sigma 3PG]}{[\Sigma GAP]} \cdot \frac{[\Sigma ATP]}{[\Sigma ADP][\Sigma Pi]} \cdot \frac{[1\text{-lactate}]}{[\text{pyruvate}]} = 1.65 \times 10^{+7} M^{-1}$$

5c. Or:

$$\text{Free Cytoplasmic } \frac{[\Sigma ATP]}{[\Sigma ADP][\Sigma Pi]} = \frac{[\Sigma DHAP]}{[\Sigma 3PG]} \cdot \frac{[\text{pyruvate}]}{[1\text{-lactate}]} \times 7.5 \times 10^{+5} M^{-1}$$

5d. Alternatively, from the creatine phosphokinase reaction (EC 2.7.3.2)

$$K_{CK} = \frac{[\Sigma ATP]}{[\Sigma ADP]} \cdot \frac{[\text{creatine}]}{[\Sigma \text{creatine-P}][H^+]} = 1.66 \times 10^{-9} M^{-1}$$

For the Pyrophosphorylation State or [ΣPPi]/[ΣPi]:
Lawson JWR, Guynn RW, Cornell NW, Veech RL. In Gluconeogenisis (Hanson RW, Mehlman MA eds) pp 481-511, John Wiley, New York, 1976

5e. From the UDPG Pyrophosphorylase reaction (EC 2.7.7.9):

$$\text{Free Cytoplasmic } [\Sigma PPi] = \frac{[\Sigma \text{glucose 1-P}][\Sigma UTP]}{[\Sigma UDPglucose] \cdot K_{UDPGPPiase}}$$

where $K_{UDPGPPiase} = 4.55$

5f. For liver and blood glucose:

$$K_{G\text{-}PPi\ Trans\ Pase} = \frac{[\Sigma \text{Glucose 6-P}][\Sigma Pi]}{[\text{Glucose}][\Sigma PPi]} = 45.9$$

5g.

$$K_{G\ 6\text{-}P\text{-}PPi\ Trans\ Pase} = \frac{[\text{free F 1,6 diP}][\Sigma Pi]}{[\Sigma \text{fructose 6-P}][\Sigma PPi]} = 29.0$$

VI Eqn 6 Determination of Osmotic Pressure —π

Van't Hoff JH. *Arch Neerl Sci* 20: 239-303, 1886

$$\pi = \Sigma[C]RT$$

where:
π ~ osmotic pressure in atmospheres (relative to pure H$_2$O)
Σ[C] ~ Σ[concentrations] of solutes in mole/liter
R ~ gas constant = 0.082 liter atmospheres/mole/degree K
T ~ 273 = ° C.

Equation 7 hereinbelow presented is described in my above referenced copending application.

VII Eqn 7 The Equation of State of the Cell

Relating the ΔE across the cell membrane, the distribution of [Na$^+$], [K$^+$], [Cl$^-$], and [Ca$^{2+}$] between extracellular fluid and cytoplasmic H$_2$O and hence cell volume to the cytoplasmic [ΣATP]/[ΣADP][ΣPi]

$$\Delta G_{Na/K\ ATPase} = \Delta G^0_{ATPase} + \Delta G^0_{ions} + RT \ln \frac{[\Sigma ADP][\Sigma Pi]}{[\Sigma ATP]} + RT \ln \frac{[Na^+]_o^3[K^+]_i^2[Cl^-]_o}{[Na^+]_i^3[K^+]_o^2[Cl^-]_i} + T\Delta S$$

Since ΔG=0, then:
0= −7.73 kcal/mol =0 =(−6.3 kcal/mole) =8.5 kcal/mole =5.5 kcal/mole $$\text{As 1 kcal/mole} = \frac{0.082 \text{ liter atmos/mole/}°K.}{1.98 \times 10^{-3} \text{ kcal/mole/}°K.} \times \frac{1}{22.4\ 1/\text{mole}} = 1.85 \text{ atmospheres}$$

then the TΔS term =5.5×1.85=10.2 atmospheres.
And further from Van't Hoff (Eqn 6)

$$\Sigma[C]_{in} - \Sigma[C]_{out} = \frac{\pi}{RT}$$

$$\Sigma[C]_{in} - \Sigma[C]_{out} = 0.40 \text{ moles/L}$$

Eqn 7 states that since U$_T$H$_2$O outside = U$_T$H$_2$O inside, the cell is prevented from swelling by the Na$^+$/K$^+$ ATPase which electroneutrally pumps out 2 mOsmoles/ATP hydrolyzed. The ΔE across the cell (membrane) is reflected by the distribution of $[Cl^-]_o/[Cl^-]_i$ in accordance with the Nernst equation (Eqn 3). The $T\Delta S$ or decreased entropy within the living cell represents the increase "order" characteristic of the living cell. See Eqn 0.

7b. From the high capacity $Na^+/Ca^{2+}$ exchanger written in an electroneutral manner reflecting the free permeability of $Cl^-$ in accordance with the dictates of the Nernst equation, (Eqn 3):

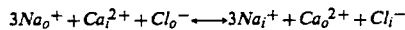

$$3Na_o^+ + Ca_i^{2+} + Cl_o^- \longleftrightarrow 3Na_i^+ + Ca_o^{2+} + Cl_i^-$$

The net osmolar movement of eqn 7a is 2 osmoles →outside. In contrast, the net movement of eqn 7b is 3 mosmoles →inside, requiring the $Na^+/K^+$ ATPase to cycle 3 times for each 2 times the $Na^+/Ca^{2+}$ exchange mechanism operates in order to maintain osmotic equilibrium.

The gradient $[Ca^{2+}]_i/[Ca^{2+}]_o$ is thus a direct function of the $[Na^+]_o^3/[Na^+]_i^3$, (the $Cl^-]_o/[Cl^-]_i$), and function of the phosphorylation and entropy state of the cell.

These equations can be readily solved either manually or by a suitably programmed computer. These interrelationships make possible various new processes since these interrelationships permit one to predict with certainty the solution characteristics which will be obtainable when practicing, for example, dialysis through an inert semipermeable membrane, such as is above, for example in hemodialysis.

Thus, and as indicated above, the present invention in one aspect provides a process for preparing an aqueous hemodialysis solution which when used in hemodialysis will produce a desired electrolyte composition in hemodialyzed blood. In such a process, one measures the approximate molar concentration of the albumin initially present in the blood of the patient to be hemodialyzed with such desired solution. Various techniques are available for measuring albumin content in mammalian blood and any convenient such technique can be employed in the practice of this invention. For example, total blood protein can be determined using a plasma sample of the patient's blood. From the total blood protein and an electrophoresis of such protein, an estimate of the albumin and globulin content of the total blood protein can be made.

As those skilled in the art appreciate, albumin is known to have a molecular weight of approximately 68,500. It has previously been established that albumin has a variable anionic charge which is dependent upon the pH of the solution wherein the albumin is dissolved (see Tanford, C. S. J. Am. Chem. Soc. 72, 441-451, 1950). For example, at the physiological pH value of 7.4, albumin has a valance of approximately 20 mEq/mole. The hydrogen ion equilibria in native human serum albumin was measured and described (Tanford, C. S. J. Am. Chem. Soc. 72, 441-451, 1950). Thus, from the published information, the valence of albumin at pH values over the physiological range are established. By selecting a particular pH value for a desired hemodialysis solution, the approximate anionic valence of albumin at this pH value becomes determined and can be estimated by the supervising physician.

Since albumin is the principal polyanionic material present in plasma (blood), and since the valence of albumin is variable according to hydrogen ion concentration (or pH), the pH of the dialysis solution contacting plasma during hemodialysis controls the pH of the plasma and the charge on the plasma albumin. The approximate molar concentration of albumin is the only knowledge about the patient's blood (plasma) that is needed in order to prepare an aqueous hemodialysis solution which will be suitable to the individual needs of a patient undergoing hemodialysis. Thus, the attending physician has the means for the first time to produce in the patient's plasma as returned to such patient after hemodialysis thereof a desired or specified composition of electrolytes which meet the special needs of that patient in an economically feasible manner which produces for less toxicity than any existing solution.

In addition to measuring the molar concentration of patient blood albumin, and in addition to selecting a pH value for the hemodialysis solution being prepared, the physician (or, perhaps, trained technician) selects initially the approximate concentration desired for each of the following specified plasma electrolyte components in the freshly hemodialyzed blood to be returned to the patient after hemodialysis of the patient's blood with the desired solution: sodium, potassium, calcium, magnesium, chloride, bicarbonate,. sigma phosphate, L-lactate, pyruvate, D-betahydroxybutyrate, and acetoacetate according to such conditions as: the reasons for dialysis, the patient's general disease, his faithfulness in following instructions, the periods between dialysis, and other such individual factors; depending upon what components are to be included in a starting hemodialysis fluid. Most importantly such fluids can eliminate many of the known pathologic consequences associated with the use of most commonly used hemodialysis fluids (see Mansell MA, Wing AJ. Brit. Med. J. 1983; 287: 308-309) without significantly increasing cost of hemodialysis.

Using the foregoing equations, the composition of the desired hemodialysis solution is then calculated after which the desired solution is prepared.

Using the above determined composition information, conventional methods of electrolyte solution preparation can be employed which are well known to those of ordinary skill in the art.

In another aspect as indicated above, the present invention provides a process for predicting accurately the plasma electrolyte content of freshly hemodialyzed mammalian blood when that blood is hemodialyzed with a hemodialysis solution of known fixed starting composition. In such process, one measures the approximate molar concentration of the albumin initially present in the blood of the patient to be hemodialyzed, as explained above in connection with the foregoing process.

Then one substitutes the concentration values for each electrolyte values in the plasma of the blood to be hemodialyzed.

The equations 2 permit one to approximate the concentrations and distributions in each of hemodialyzed blood and hemodialysis solution.

Illustrative programmed solutions of equation 2 are now described.

Figure 1B:
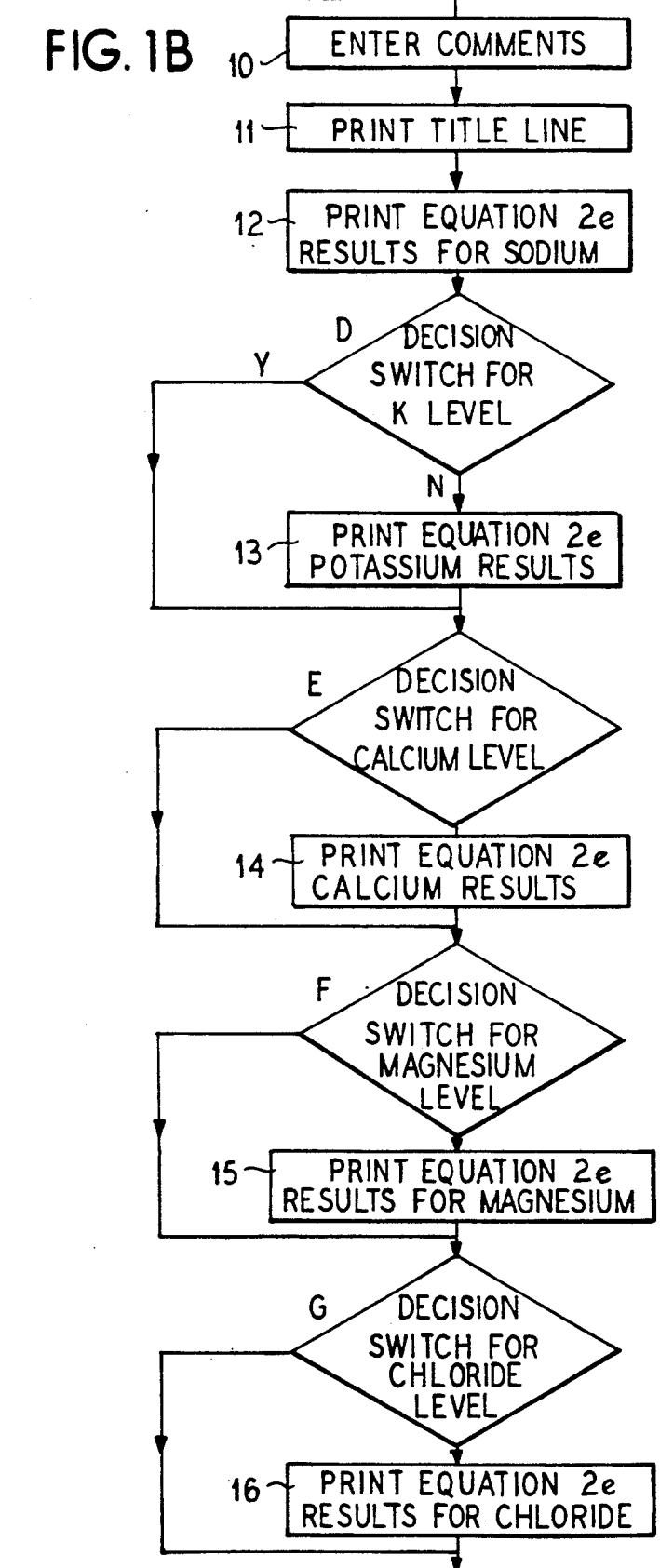
Figure 1C:
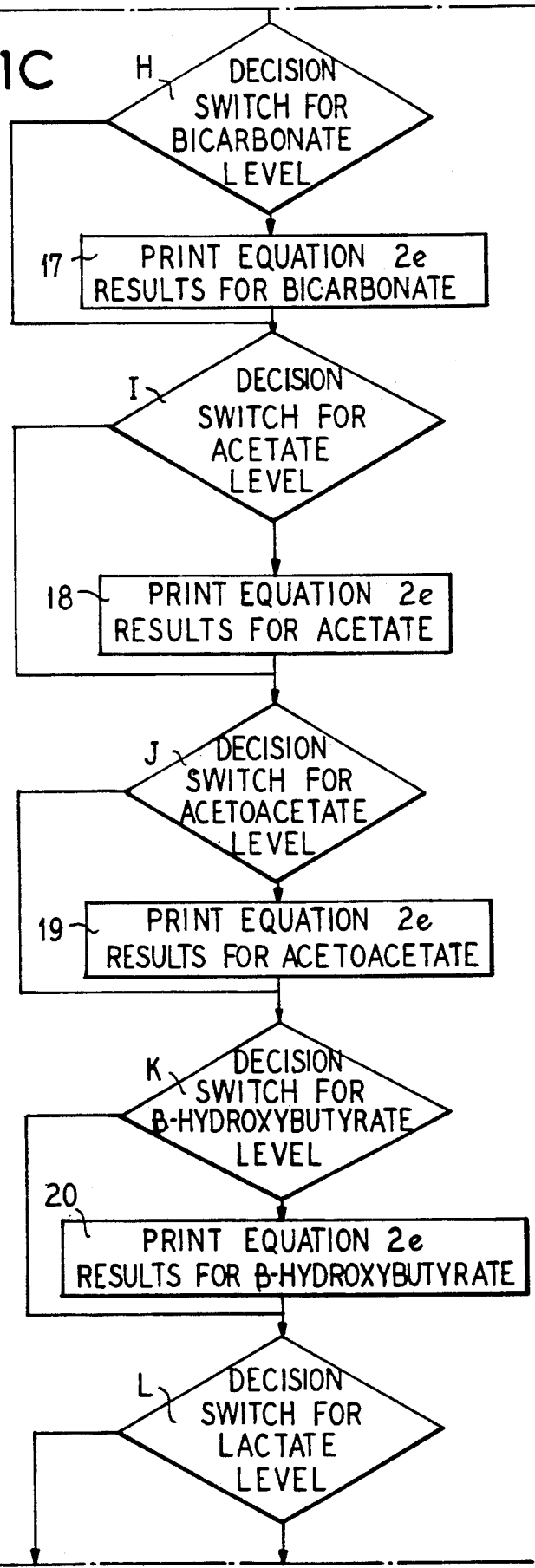

Referring to FIG. 1, it is seen that, when one desires to determine the electrolyte composition of the plasma returning to the patient using any given hemodialysis fluid using equation 2 (above), one initially determines the actual electrolyte composition of the hemodialysis solution to be used. Thus, one determines the identity of each electrolyte present and its respective quantity (concentration in millimoles per liter) in the hemodialysis starting solution. As indicated, the cations present in this solution will usually comprise from two to four metals selected from the group consisting of sodium, potassium, calcium and magnesium, while the anions present in such a solution will typically comprise chloride and possibly bicarbonate and inorganic phosphate. The designation "Pi" is used herein, for convenience, to designate inorganic phosphate ions. As those skilled in the art appreciate, the valence of Pi at pH 7.4 is taken, for exemplary purposes herein, to be $-1.8$/mole.

Also, as disclosed herein, a dialysis starting solution may contain dissolved therein any one of three different near equilibrium couples (identified respectively as bicarbonate anion and $CO_2$, L-lactate anion and pyruvate anion, and D-betahydroxybutyrate anion and acetoacetate anion). Thus, all of the individual electrolyte types and concentrations are entered into the computer being used in a convenient first step toward achieving the desired estimate of final plasma electrolyte composition.

Next the computer, duly programmed, calculates the total anionic charges present in the starting hemodialysis solution using equation 2b1. The computer is programmed to produce this total from the use of equation 2b1 above presented.

Next, the operator enters into the computer the albumin molar concentration and charge existing in the blood of the patient to be hemodialyzed. The estimation of patient molar albumin concentration is accomplished by routine hospital laboratory procedure. The anionic charge associated with the patient's albumin is determined by the patient's plasma pH. (Tanford, ref cited above.) Equation 2b2 is then a statement of electrical neutrality in the plasma.

The foregoing operations are illustrated in FIG. 1 as process boxes 1, 2, and 3, respectively. Next, the computer is set to solve sub-elements of equation 2e, knowing the relationships in 2c and 2d. Thus those elements which are present in the starting hemodialysis solution (identified by the subscript "o") are entered into equation 2e and the equation 2e solution is carried forward thereafter as far as possible based upon the existing molar concentration of cations and anions in the actual starting hemodialysis solution, all as summarized by process box 4 in FIG. 1. The result of the calculations thus performed in process box 4 are passed into process box 5 where calculations proceed further to the extent permitting achievement of a temporary solution to equation 2e as shown in process box 5.

Next, a decision point, designated as "A", is reached for adjustment of sodium level. In the present illustrative program embodiment, the decision switch "A" is set to produce a minimum of one recalculation for equation 2e. Thus, the signal received by switch "A" is fed into process box 6 where an initial adjustment of sodium level in equation 2e is undertaken using a predetermined sodium factor. The result of the calculation in process box 6 is fed back into process box 5 where a new, tentative solution to equation 2e is reached.

Thereafter, there is a return to decision switch "A" which, at this point, permits the signal to be passed through to process box 7 wherein a temporary absolute value for equation 2e is calculated.

Thereafter, the signal is allowed to flow through to decision point or decision switch "B" where a determination is made as to whether or not the initial tentative solution in process box 5 is less than the adjusted tentative solution to equation 2 achieved in process box 5 on the second pass there through. If the initial solution to equation 2e is less, in fact, than the second solution to equation 2e, then the signal is shunted into process box 8 where a register reset for the temporary absolute value of equation 2e is calculated. The program flow from process box 8 next occurs back to process box 6. Then, in process box 6, the repetitive recalculation above described occurs and the cycle is repeated. The reiterative process is continued until an immediately prior solution to equation 2e is finally found to be equal to or greater than a current temporary solution to equation 2e. When this occurs, the signal is fed into decision switch "C" for comparison of a temporary absolute value of equation 2e against an acceptable deviance.

From switch "C", the signal is permitted to move to process box 9, when and if the absolute value of equation 2e is equal to or greater than the accepted, predetermined, deviant or constant. In process box 9, the sodium adjustment factor is reduced by a predetermined selected quantity or factor after which the signal is returned to process box 5 where a new, tentative equation 2e solution is produced. This procedure is then continued through the loop described until decision switch "C" shows that an immediately preceding solution to equation 2e is within the acceptable (predetermined) deviant or constant.

In the present program, the final output from decision switch "C" is fed to process box 10 where comments, as from a physician or technician, are conveniently entered. The comments entered generally relate to the results displayed, as those familiar with the art will readily appreciate. From process box 10, the signal passes into process box 121 where a title arrangement is printed (or displayed, if desired).

Next the signal is fed to process box 12 where equation 2 results for sodium are printed (or displayed, if desired). The signal is then passed to decision switch "D". In decision switch "D", equation 2 results are checked for potassium level. If the potassium level is zero, then it is not printed as in a subsequent process box 13. On the other hand, if the potassium level is other than zero, the process box 13, is activated and the potassium detail is printed. Thus, the equation 2 results for potassium are printed (or displayed, if desired).

A similar procedure to that just described, with respect to potassium, is then pursued with respect to calcium in decision switch "E" and process box 14, with respect to magnesium in decision switch "G" and process box 16, with respect to bicarbonate in decision switch "H" and process box 17, with respect to acetoacetate as shown by decision switch "J" and process box 19, with respect to betahydroxybutyrate as shown by decision switch "K" and print box 20, with respect to lactate as shown b decision switch "L" and process box 21, and finally, with respect to pyruvate as shown by decision box "M" and process box 22.

The patient's albumin concentration and charge is printed or displayed by process box 23, after being entered by the physician (see box 3).

Process box 24 marks the end of processing and completion of the program.

Figure 2D:
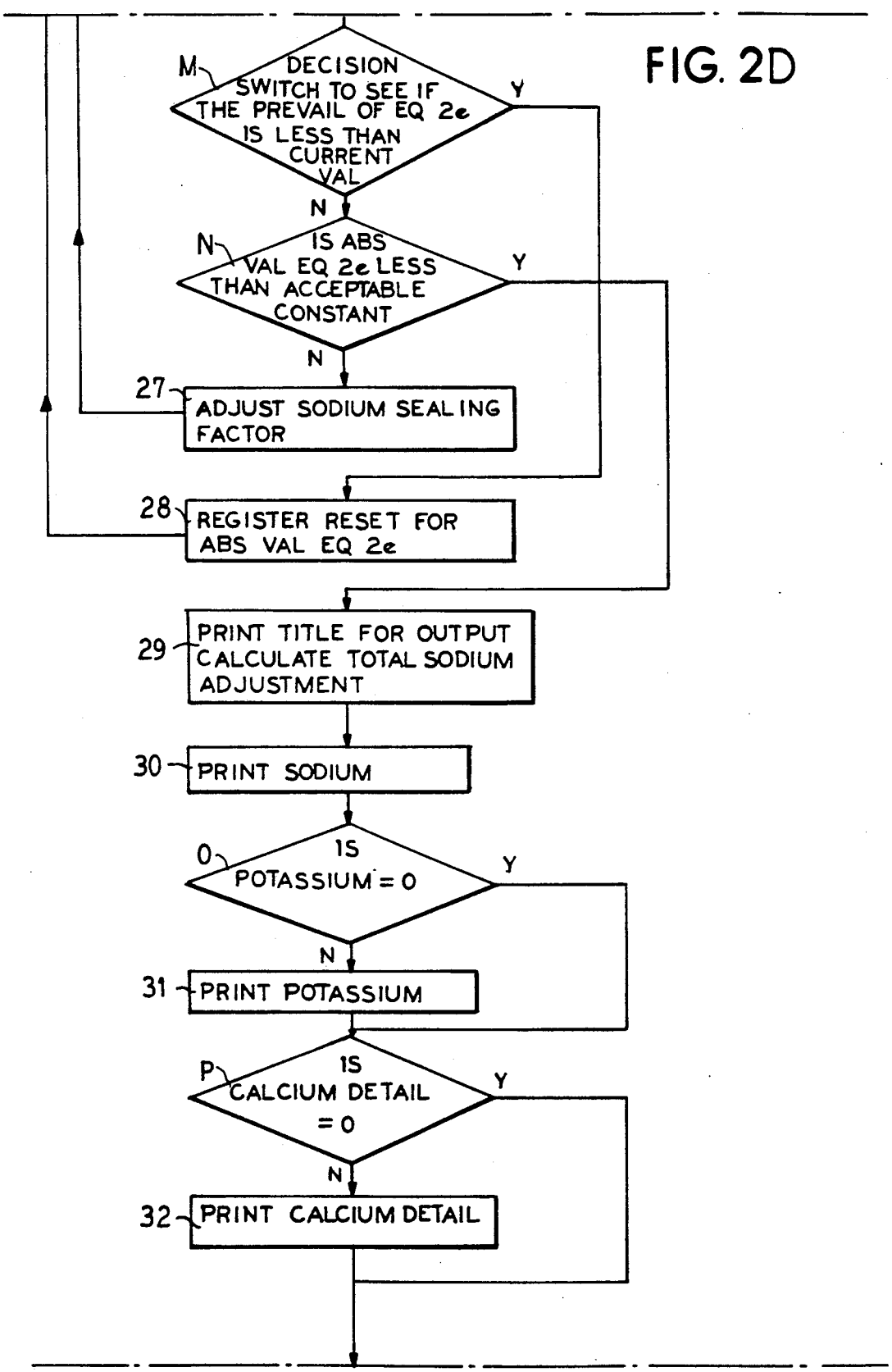
FIG. 2 (sheets A, B, C, D, E, and F) illustrates one embodiment of another computer program which can be used for solving the multicomponent interrelationships herein presented the present program being capable of identifying the composition of a hemodialysis fluid to be used for the hemodialysis of a patient based upon the desired or anticipated patient plasma electrolyte composition of the freshly hemodialyzed blood of that patient.
Figure 2E:
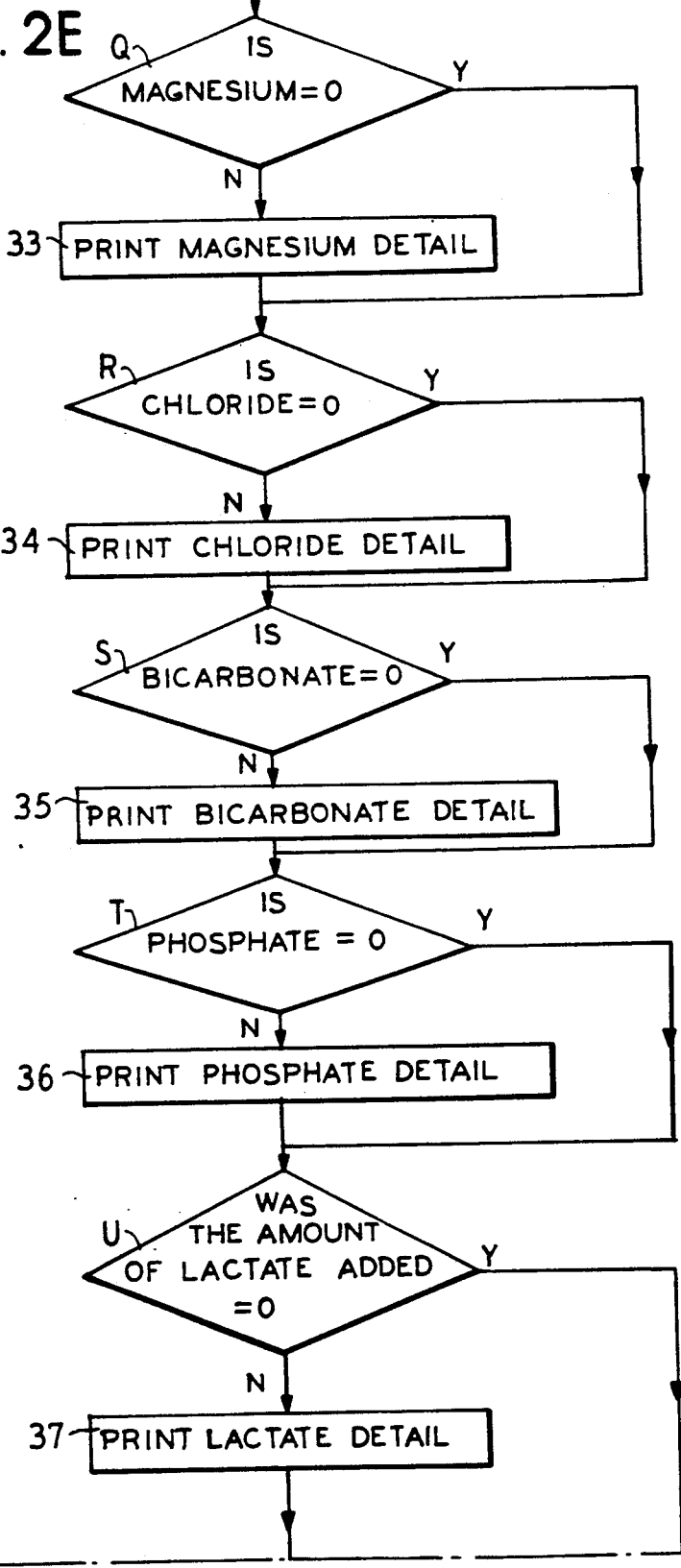

Referring to FIG. 2, in order to provide a particular hemodialysis fluid for use with a particular patient, one may utilize a program such as is shown in FIG. 2 and as is herein described in the accompanying text:

Initially, one enters desired individual electrolytes (in millimoles/L plasma and their concentrations desired in the final dialyzed blood returning to the patient in the program. In this program, the cations (sodium, potassium, calcium or magnesium) are first input, as shown in process box 1, and thereafter their levels are calculated as millimoles/L plasma $H_2O$ to correct for water volume using the constant of 0.935 ml $H_2O$/ml plasma which is a value typical for plasma; this adjustment is accomplished in process box 2.

Thereafter, total cationic charges are calculated using equation 2b2 above shown, as shown by process box 3. This calculation is accomplished by using the charges of the quantities of cations employed (as shown in process box 1).

Next, the individual molar concentrations of the various anions desired are entered (as shown in process box 4). These anions, which may be regarded as reasonably typical, comprise chloride, bicarbonate and inorganic phosphate.

Thereafter, as was done with the cations, the levels of the anions are adjusted with the constant 0.935 ml $H_2O$/ml plasma to correct for water volume, all as shown in process box 5.

Next, total anionic charges are calculated by summation, as shown in process box 6.

The albumin molar concentration and charge associated with the particular patient who is to be hemodialyzed are then entered into process box 7. The charge to be given the albumin, typically between $-5$/mole albumin at pH 5.5 or $-30$/mole albumin at pH 8.4 is chosen by the physician. This choice determines the pH (and $HCO_3^-/CO_2$ ratio) of the dialysis fluid in accordance with the Henderson-Hasselbalch equation (equation 1). The value of $Z$ [Prot-$^{-z}$] is needed to solve equation 2b2 (see box 8)*.

It follows from eqn 2b2, that if the Z[polyion $^{z+}$] is added to dialysis fluid, the relationship in eqn 2 simply has the Z[polyion$^{z+}$] term on both sides. In the special case where Z[prot$^{z-}$]o the $[Na^+]_i/[Na^+]_o=1$, the electrolyte concentrations in this special case becomes the same on both sides of the membrane.

Next, the total anion charges are adjusted with the albumin molar concentration and charge, as shown in process box 8; after which the total charge of anions is subtracted from the total charge of cations, as shown in process box 9.

At this point, decision switch "A" is activated. If the absolute value of the difference shown by process box 9 is less than a predetermined fixed value, then the difference is set to zero, as accomplished in process box 10. If the difference is greater than the predetermined value, then program flow proceeds from switch "A" to switch "B". It is necessary to have the total charges of cations equal the total charges of anions because of the law of electrical neutrality. In the present program, if electrical neutrality has been achieved by equivalence between anion and cation charges, or if the difference is so small there between as to be considered acceptable (negligible), then the program flow proceeds to decision switch "B". In effect, if anions are not equal to cations in charge, then by setting the difference arbitrarily to zero in process box 10, decision switch "B" is skipped, or is set to "true", thus postponing a decision as to the manner in which the difference existing between anion and cation charges is to be handled until a later point in this program.

If the total of anion charges is greater than the total of cation charges, then, as shown by decision point "C", electrical neutrality is not achievable and process box 11 is activated wherein an error message is displayed or printed and also wherein program flow is returned back to process box 1 for re-entry of new and altered (corrected) values of cations.

If anion charges are not greater than or are not equal to cation charges, then process box 12 is activated. Here the technician is informed that there is an anion deficit in the plasma make-up or composition. And such technician or physician is asked if he wishes to make up the difference with a near equilibrium couple such as 1-lactate and pyruvate anion mixture.

If the operator makes the decision to include 1-lactate and pyruvate, then decision switch "D" permits the program to flow through to process box 13. If on the other hand, the decision of the operator is not to include lactate/pyruvate mixture, then decision switch "D" bypasses process box 13, 14, 15, and 16 (and their associated decision switches E, F, and G are bypassed).

In process box 13, if such is activated, the operator is asked to enter his total chosen concentration of lactate/pyruvate mixture in an amount sufficient to achieve electrical neutrality in the contemplated or desired electrolyte solution being formulated. After this information is input by the operator the program proceeds to decision switch "E". Here a computer check is made of the input achieved in process box 11. If electrical neutrality is in fact achieved, then process box 15 is activated. If on the other hand, if electrical neutrality is not produced by the input in process box 13, then decision switch "E" activated process box 14. In process box 14, an error message is printed and the operator is asked for corrected instructions to be input back into process box 13. This process is repeated until the amount of lactate/pyruvate entered is sufficient to produce electrical neutrality.

In process box 15, in effect the anion gap is filled with the adjusted molar concentration of lactate/pyruvate selected in process box 15.

Next, decision point F is activated. Here one tests to see whether or not the adjusted anion gap is within acceptable limits. If this adjustment is not acceptable, one passes from decision point F to decision switch G and on through to process box 17. On the other hand, if this adjustment is satisfactory (within defined limits), then process box 16 is activated, and this process box sets the anion gap to zero, whereupon the process flow proceeds into decision switch G.

In decision switch G, a decision is made as to whether or not electrical neutrality has in fact been achieved. If electrical neutrality has not been achieved, then the program flow proceeds on through into process box 17. If, on the other hand, electrical neutrality has been achieved, then the program flow proceeds from decision switch G to process box 23. In process box 17, if electrical neutrality has not been achieved, then the operator is notified by a print, and the operator is asked if he wants to make it up with acetoacetate anion and betahydroxybutyrate anion. If the operator affirmatively indicates that he wishes to add a mixture of acetoacetate and d-betahydroxybutyrate, then the program proceeds through decision switch H into process box 18. On the other hand, if the operator chooses not to add any mixture of acetoacetate and betahydroxybutyrate, then decision switch H passes the control to process box 22. In effect, decision switch H controls the decision is to be compensated with a mixture of acetoacetate and betahydroxybutyrate or not.

Process box 18 asks the operator a question to the effect: "Since you want to include a mixture of acetoacetate and betahydroxybutyrate, how much of such mixture do you wish to add?"

From process box 18 the program is sent to decision switch I, wherein a decision is made: "Is the quantity of ketone bodies added greater than what is needed to satisfy the anion gap?" If it is, then decision point I activates process box 19, and an error message is printed for the operator and also control returns to process box 18, where the operator must input appropriate corrections. When the amount is equal to or less than the anion gap, decision point I activates process box 20 and in process box 20 the anion gap is filled with the amount of ketone bodies entered in process box 18.

Program flow now enters decision point J wherein a decision is made to see whether or not the anion gap is within acceptable limits. If it is, then process box 21 is activated and the anion gap is set to zero. If on the other hand, if it is not then the process flow proceeds directly to process box 22 passing through decision point K. In decision point K, a decision is made: "Is the anion gap zero?" If it is, then process flow proceeds directly from decision point K to process box 23. If it is not, then process flow proceeds from decision point K to process box 22.

In process box 22, a print occurs wherein the operator is informed that there still remains an anion deficit in the proposed plasma composition, and further the operator is asked: "What ion do you wish to use to make up the remaining deficit?"

Once a decision has been made by the operator concerning matters raised in process box 22, process will proceed to process box 23 wherein a display is made showing the entire plasma composition.

From process box 23, the program proceeds to process box 24, where a temporary value for equation 2e is calculated. It is observed that the present use of equation 2e is, in effect, the inverse of the use of equation 2e which was employed in the practice of the program in FIG. 1 above.

From process box 24, program flow enters decision switch L. Decision switch L forces a second temporary calculation of equation 2e. Thus in the first iteration program flow passes to process box 25 for an adjustment of sodium level (by a predetermined amount). Then, process flow control returns to process box 24 where recalculation of the temporary value or solution for equation 2e is achieved. Program control then passes through process box 24 to decision point L, and from decision point L through process box 26. In process box 26, an absolute value or solution to equation 2e is determined.

In decision point M, a decision is made as to whether or not to test the previous value (or temporary value) of equation 2e against a new temporary value for equation 2e. To meet the yes condition, the previous temporary value of equation 2e must be less than the currently determined value of equation 2e. If the decision in "no", then program control passes to decision switch N.

In decision point N, the computer asks: "Is the absolute value of equation 2e less than an acceptable (preset) constant?" If the answer is yes, then program control proceeds to process box 29. If the answer is no, then program control proceeds to process box 27.

In process box 27, the sodium scaling factor (which is a predetermined constant) is incrementally adjusted, after which program flow returns from process box 27 to process box 25 and a new absolute value for equation 2e is achieved.

Process box 28 involves the use of a register reset of the absolute value for equation 2e whereby process flow returns to process box 28 in an iterative mode continues until decision switch N produces a yes. When this occurs, then process box 29 is activated.

In process box 29, the program output title is printed (and optionally displayed). Also, in process box 29 the sodium value is reduced by 0.935, which is the water adjustment factor. Thus the total sodium adjustment is known.

Next, in process box 28, a count of the sodium detail line is printed (and optionally displayed).

Next, in decision point 0, the computer asks if the potassium molar concentration is zero or not. If this concentration is not zero, then the potassium level is printed in process box 31. A similar sequence of decision points and print details occur for each of calcium, magnesium, chloride, bicarbonate, and phosphate, all as shown below.

| Ion | Decision Point | Print Process No. |
|---|---|---|
| $Ca^{++}$ | P | 32 |
| $Mg^{++}$ | Q | 33 |
| $Cl^-$ | R | 34 |
| $bicarbonate^-$ | S | 35 |
| sum phosphate$^{-1.8}$ | T | 36 |

Then, next, in decision point U, the question is asked: "Was the quantity of mixture of lactate plus pyruvate zero?" If the answer is yes, then process flow proceeds from decision point U to decision point Z. If no, then process flow proceeds from decision point U to process box 37, where a lactate quantity is printed. Then next, process box 38 is activated where a pyruvate is printed (and/or displayed if desired).

Thereafter process control passes to decision point V where a decision is made as to whether or not the quantity of mixture of betahydroxybutyrate and acetoacetate is zero or not. If zero, then process control passes on through to decision point W. If not, successively, process boxes 39 and 40 ar activated, wherein, respectively, betahydroxybutyrate detail is printed followed by the printing of acetoacetate detail.

In decision point W a decision is made as to whether or not the ion gap has been closed. If so, then program control proceeds through to process box 42. If not, then the process box 41 is activated and process box 41 prints the identity of the particular ion to be used to fill the anion gap.

In process box 42, the computer prints (and/or displays, if desired) the value of plasma albumin (in terms of molar concentration) and albumin charge (z).

In process box 43, the program is terminated.

The Rate of Change in Electrolyte Concentration

By regulating the rate of change in plasma electrolyte composition during, for example, hemodialysis, one can also minimize and even eliminate the so-called disequilibrium syndrome and effects associated with the occurrence thereof in a patient.

The disequilibrium syndrome is believed to be associated with rapid changes in a patient's electrolyte and tissue $H_2O$ composition during the course of hemodialysis. Thus, when a patient is hemodialyzed with a dialysis fluid having an electrolyte composition which is different from the patient's own plasma, the patient's electrolyte composition changes, and approaches the composition of electrolytes in the fluid being used for the hemodialysis. Freshly hemodialyzed blood is returned to the patient and mixes with the patient's blood. Over the time period of the hemodialysis, measurable and significant alteration of the patient's blood (plasma) electrolyte composition results. As the patient's electrolyte composition changes, many things in a patient also change concomitantly, including, for examples, distribution of $H_2O$ between the various compartments (as reflected in plasma, extracellular fluid, and intracellular fluid), and patient's blood urea content. When these changes in patients blood electrolyte composition occur rapidly, it is now believed that the disequilibrium syndrome becomes observable, with consequences, which can be severe, for patient comfort. Thus, much discomfort that patients experience during hemodialysis is believed to result from the rapid changes in electrolyte and water concentration within the various body water compartments.

It is customary in conventional hemodialysis to run the same dialysis fluid during the entire three- to five hour period. The shape of the curve of the relationship change in concentrates of any substance in a patient's body fluids in relation to time is therefore given by a first order rate equation derived from the general equation for exponential decay. Thus:

$$C_{at\ any\ time} = C_o e^{-(0.693t/t_{\frac{1}{2}})}$$

where:
C is approximately equal to the concentration of any substance in the patient's blood (plasma) at any time;
$C_o$ is approximately equal to the initial concentration of such substance in the patient's blood;
e is the number whose natural logarithm = 1, which number is about 2.718
t is approximately equal to the time elapsed from the start of hemodialysis;
$t_{\frac{1}{2}}$ is approximately equal to the time required to achieve a change of one half the value of the initial concentration (in comparison to the anticipated or desired final concentration).

Figure 3:
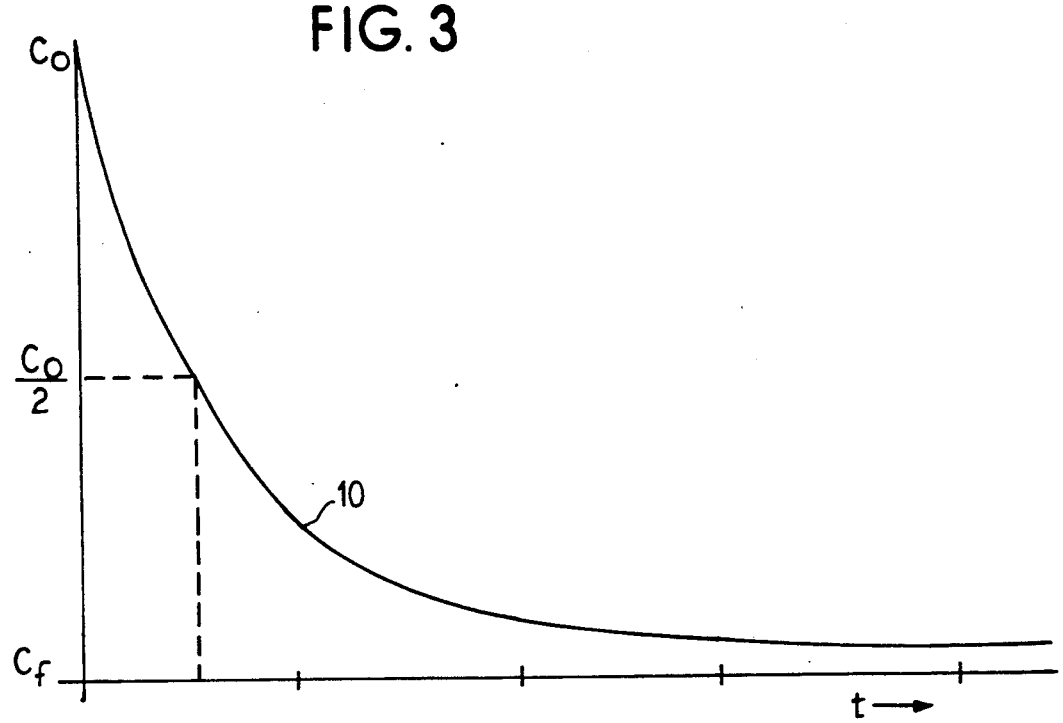
FIG. 3 is a diagrammatic plot of change in concentration of one diffusible component of the patient's plasma as ordinates versus time as abscissae (the plot illustrates a first order rate equation)

The final form of the curve produced by plotting equation (1) (above) is illustrated in FIG. 3. Referring to FIG. 3 the curve 10 is seen to be hyperbolic in form. The point where the concentration is midway between $C_o$ (initial concentration) and the final concentration ($C_f$) (shown at the intersection of abscissa and ordinate in FIG. 3) is shown in FIG. 3 as $C_o/2$. The time ($t_{\frac{1}{2}}$) required to achieve $C_o/2$ is thus seen to be a minor fraction of the total elapsed time t, the time $t_{\frac{1}{2}}$ being shown with a dotted line in FIG. 3. The rate of change after the time when $C_o/2$ is achieved is considerably slower than the rate of change which occurs between $C_o$ and $C_o/2$.

When equation 1 is rewritten in natural log (ln) form, the equation (1) becomes:

$$\ln C = \ln C_o e^{-(0.693t/t_{\frac{1}{2}})}$$

where:
C, $C_o$, t, and $t_{\frac{1}{2}}$ have their above defined meanings.

Figure 4:
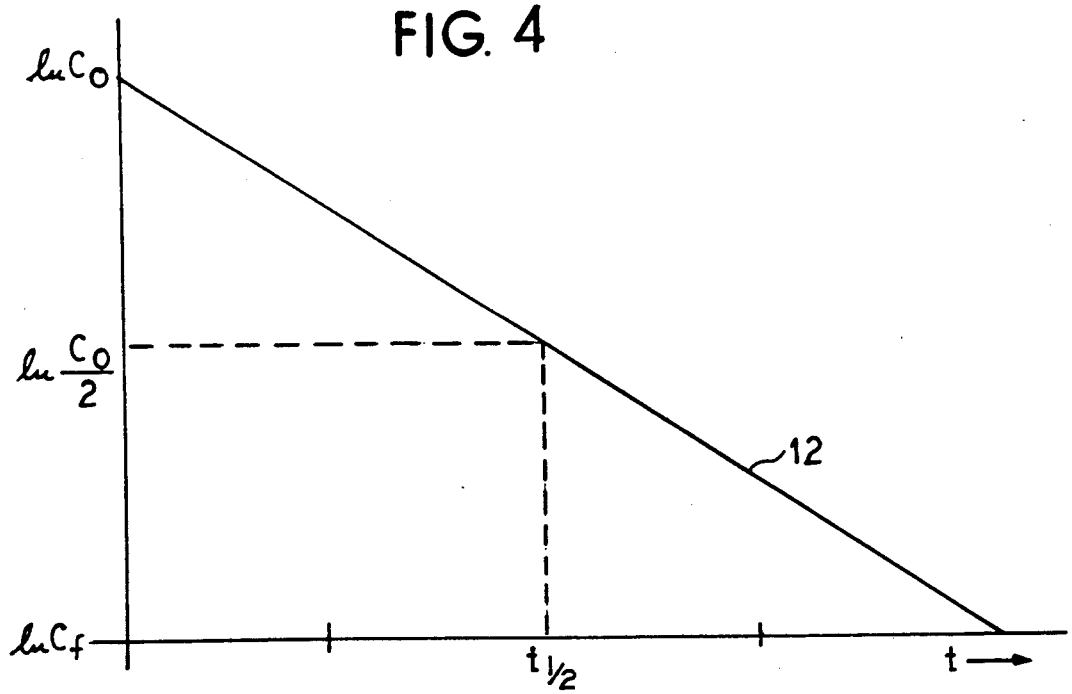
FIG. 4 is a diagrammatic plot, similar to FIG. 3 except concentration is plotted as the natural logarithm.

The general form of the curve resulting when equation (9) is plotted is shown in FIG. 4. Here, the shape of the rate of change in concentration is shown by line 12. The shape of line 12 is linear.

By lengthening the time required to reduce the initial concentration, the problems associated with patient discomfort and disequilibrium syndrome are eliminated or reduced substantially It is advantageous for a patient's feeling of well-being to convert the rectangular hyperbolic function (or change) shown in FIG. 3 to the linear function (or change) shown in FIG. 4, so as to minimize the rapid changes occurring during the first part of hemodialysis and so as to make the changes uniform throughout the entire period of dialysis If effect, the rate of change of concentration $C_o$ is altered from that shown by curve 10 in FIG. 3 to that shown in FIG. 4 by plot 12.

Figure 5:
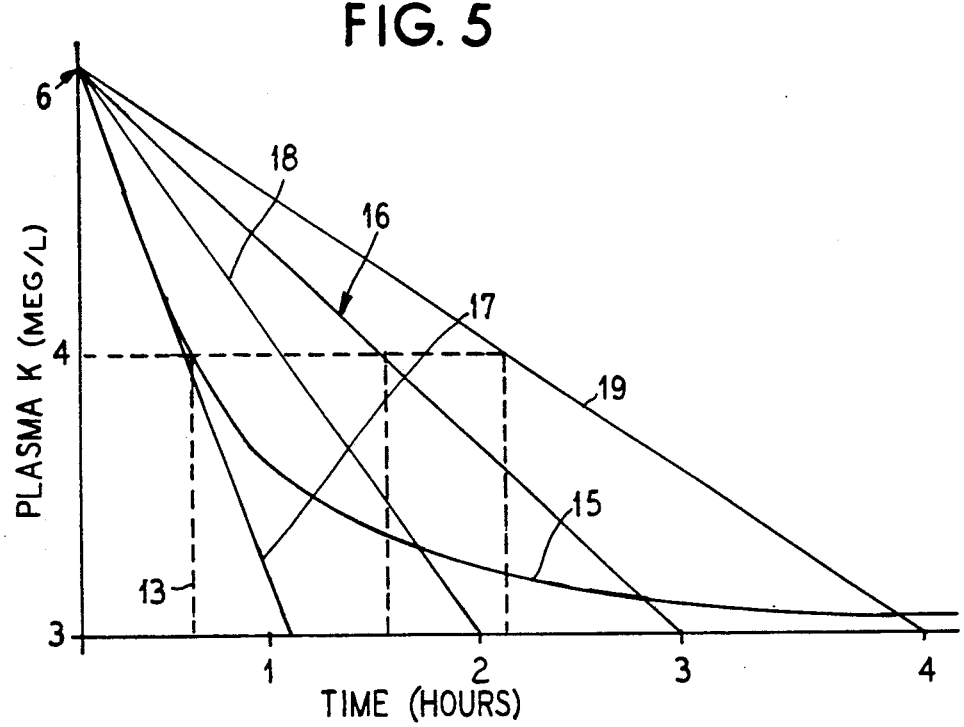
FIG. 5 is an illustration of various rates of change for one diffusible component here potassium (K), in a patient's blood undergoing hemodialysis, the plot for any given rate of change being dependent upon whether the rate of change is accomplished linearly or hyperbolically.
Figure 6:
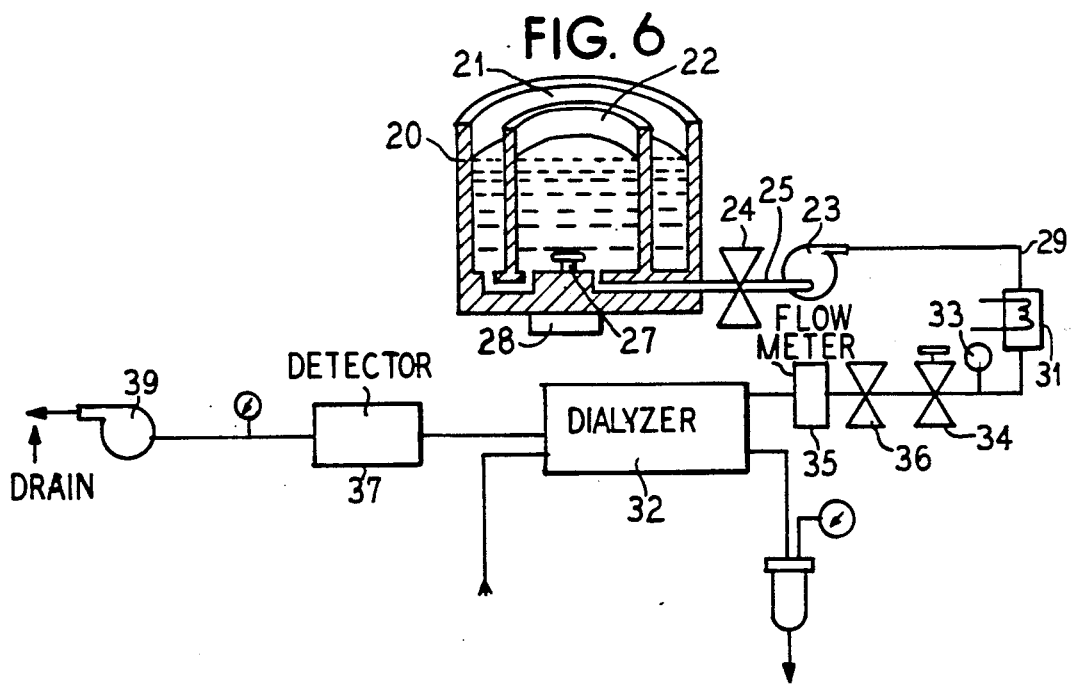
FIG. 6 is a diagrammatic illustration of one embodiment of apparatus suitable for the practice of the present invention when one desires to continuously vary the electrolyte composition of a hemodialysis solution being used for hemodialysis during the time period of that hemodialysis involving the blood of a given mammal, thereby to linearize the rate of change of composition of the plasma electrolytes of that mammal during such hemodialysis.

Referring to FIG. 5, there is seen an example of the situation which exists in conventional hemodialysis. In this example, time is shown along the abscissa while the ordinate is used to show, for this illustration, the level of plasma potassium (K) in milliequivalents per liter. The patient is assumed to have an initial plasma level of 6 mEq/1, and the patient is to have a final plasma level of 3 mEq/1. Here, the $C_o$ level is 6 mEq/1 for potassium. The time $C_o/2$ required to achieve plasma K of 4.5 mEq/L is marked by dotted line 13 when the change in concentration rate follows that shown in the first order rate equation curve 15. By using an apparatus as shown in FIG. 6 where K concentration in chamber 22 is 6 mEq/L and that in chamber 21 is 3 mEq/L, the change in concentration rate is linearized and the plot 16 shown in FIG. 5 results, wherein a substantial increase in the time $t_{\frac{1}{2}}$ can be realized. Such variability is believed to be desired from a physician's standpoint in determining the treatment to be given to a given patient Thus, under circumstances, a patient could be hemodialyzed in a very short interval of time by following a slope similar to that shown in line 17. Other possible slopes achievable with the apparatus in FIG. 6 are shown in FIG. 5. The other non linear relationships between time and concentration may be achieved if desired by the FIG. 6 or like apparatus.

Any convenient means may be employed to practice the process of the present invention with regard to achieving a desired linearization of the change in concentration of plasma relative to hemodialysis with a pre-chosen hemodialysis fluid. For example, such a rate change in hemodialysis may be accomplished by associating a mixing device with existing dialysis equipment. While any convenient such device may be employed, a simple embodiment is shown in FIG. 6 in association with hemodialysis equipment. The mixing device is herein designated by the numeral 20 and is seen to incorporate two chambers, 21 and 22, respectively. The apparatus employed is obtainable commercially from Bethesda Research Laboratories, Inc., in Rockville, Maryland, under the trade designation "BRL Gradient Former". The chamber 22 and the chamber 21 are cylindrical in configuration with chamber 22 being generally coaxial with respect to chamber 21; thus, the outer walls of chamber 22 conform the inner walls of chamber 21.

An initial hemodialysis fluid or solution which approximates in composition the patient's initial plasma composition is charged into chamber 22 at predetermined fill level so that the weights of the two solutions are equal. Chamber 21 is filled to a similar level with a hemodialysis solution composition which preferably is slightly lower in electrolyte content than the physician wishes to have at the termination of hemodialysis. Dialysis then proceeds as is described in apparatus in CRC

*Critical Reviews in Biomedical Engineering* 9, 201–244, 1983.

When pump 23 is actuated and valve 24 is opened, fluid through line 25 commences. The fluid in line 25 is comprised of a mixture of the respective fluids in chambers 21 and 22. The composition in line 25 continuously changes as fluid drains from gradient former 20, with the fluid composition in line 25 forming a linear gradient such that the rate of mixing of fluid in chamber 21 with the fluid in 22 is essentially linear as represented by, for example, one of the linear plots 16, 17, 18, or 19 in FIG. 5. In order to keep the composition of the fluid in line 25 uniform, appropriate mixing procedures can be employed. For example, a magnetic stirrer 27 actuated by a magnetic stirring plate 28 are provided for the apparatus 20 in the embodiment shown.

The output from the pump 23 is fed through a line 29 to a dialyzer unit 32, which may be of the conventional type; for example, a hollow fiber dialyzer, or the like. The fluid in line 29 passes through a heater 31, which maintains the temperature in line 29 at a predetermined value. The temperature gauge 33 is provided for monitoring fluid temperature. A throttling valve 34 is employed to regulate flow rate at the line pressure associated with fluid in line 29. A flow meter 35 is incorporated into the system for monitoring purposes. A safety valve 36 is provided conventionally. Thus, the dialysis delivery system shown delivers dialysis to hemodialyzer 32 under appropriate conditions of concentration, temperature, pressure, and flow, and monitors and alarms (not detailed) are incorporated into the system to measure and/or control hydrostatic pressures across the dialyzer membrane for fluid removal. They also safeguard against dialyzer blood leaks (as with the aid of a blood leak detector 37) and sudden changes of pressure in the blood circuit associated with separations and/or clotting The blood circuit is of conventional design and operation and is not detailed herein. Typically, in the delivery system for the blood, a blood pump, heparin infusion, and air/foam detector are preferably built into the system with provisions for appropriate connections to, and positioning of, the blood tubing. The design utilized in FIG. 6 is of the single pass, single patient system type. After the dialysis fluid leaves the dialyzer 32, it is discharged into a drain by a dialysate flow pump 39. Those skilled in the art will appreciate that no particular criticality is associated with the particular configuration of the dialysate delivery system employed for the practice of the present invention. Likewise, those skilled in the art will appreciate that many different arrangements are possible in order to obtain the desired linear gradient for the feed of dialysis fluid to dialyzer in the course of an actual hemodialysis.

If desired, the above described gradient former can be replaced by a device which produces an output at a constant flow rate and variable composition. One such device is available commercially from Waters Associates, Inc., of Milford, Massachusetts, under the trade designation Model 660 solvent programmer. In this device, a pump B delivers a predetermined outflow which is less than the total volume of flow desired. Pump A produces a flow or fluid volume which is equal to the total outflow minus the flow rate of pump B. Thus the total flow is a composite of the flows from each of the respective pumps A and B. The pumps A and B are themselves controlled by a programmer which permits one to adjust the composite flow rate and composition so that, for example, the flow rate can be constant but the composition variable This device can be used for the purpose of obtaining the desired linearity associated with the practice of the present invention.

Alternatively, and preferably, in FIG. 7 is given a rudimentary outline of a device with multiple entry points for concentrates which can be mixed in accordance with the concentrations dictated by equation 2 herein. The beginning and ending concentrations of the dialysis fluid need not be the same. Thus, any shape of curve may be obtained by appropriate programming The curve can be linear as in FIG. 5.

In use, the dialysis fluids can not only be varied during administration to achieve the desired rate of change, but also may have different compositions depending upon the attending physician's evaluation of a patient's particular needs In a particularly preferred aspect of the present invention a non-permeant (impermeant) charged material of variable charge in the solution being dialyzed is used so as to create a Donnan equilibrium situation of a variable and controllable intensity wherein the distribution of the activity of the permeant ions on both sides of the dialysis membrane may be controlled, and thereby, the ionic composition of the dialyzed fluid is regulated. Although this aspect of this invention has a wide variety of applications, it is particularly well suited for use in hemodialysis where the charges on the impermeant materials in the blood (particularly albumin, but also to a lesser extent the blood cells themselves and to an even lesser extent the globulins have charges which can create a Donnan effect) are used to create the ionic composition of the blood itself Thus, the ionic composition of a dialyzable fluid such as blood is regulated by the ionic composition of the dialyzing fluid and the charge on the impermeant charged material in the dialyzable fluid so as to determine the concentration of permeant ions in the dialyzable fluid being dialyzed.

Thus, the charge of said non-permeant charged material in said dialyzable fluid is regulated by varying at least one of the following:
(a) the pH of said dialyzing fluid,
(b) the temperature of said dialyzing fluid,
(c) the ionic strength of said dialyzing fluid,
(d) the concentration of polyvalent ions which specifically bind to said material, and
(e) the concentration of permeant materials in the dialyzing fluid which are capable of binding to the impermeant charged material being dialyzed in such a way so as to vary the charge associated with said non-permeant charged material.

Preferably, such dialyzable fluid comprises blood of a mammal, and the charge associated with non-permeant charged material in said blood is so regulated by:
(a) varying the pH of said dialyzing fluid,
(b) varying the divalent cation concentration in the dialyzing fluid,
(c) varying the concentration of permeant agents such as fatty acids in the dialyzing fluid which alter the charge on the impermeant charged material in the fluid to be dialyzed, and
(d) varying (a), (b), and (c).

The term "permeant", "permeable" or the term "diffusible" as used herein has reference to the fact that a substance or material is able (when in solution or dispersion) to pass through a membrane, such as a dialysis membrane.

Compositions

An illustrative class of electrolyte solutions usable for hemodialysis, whose compositions are determined by applying equation 2 can be characterized as shown in the following Table IV. In solving equation 2, each patient's albumin molar concentration and charge is determined, and decisions are made respecting the concentrations of individual electrolytes desired in the patients plasma at the termination of hemodialysis, as indicated above.

While the compositions of the dialyzing solutions can be conventionally prepared by hand from available salts metals, gases and the like, the apparatus provided herein permits automatic preparation of some general solutions which are designed to meet the specific needs of particular patients from those specific groups which comprise the major groups undergoing hemodialysis

TABLE IV

| Component | broad | Quantity Range (millimoles per liter) preferred |
|---|---|---|
| Total cations (mEq) | about 130 to 170 | 137–151 |
| (1) sodium$^+$ | about 130 to 155 | 135–143 |
| (2) potassium$^+$ | about 0 to 6 | 0–4 |
| (3) calcium$^{2+}$ | about 0 to 3 | 1–1.5 |
| (4) magnesium$^{2+}$ | about 0 to 2 | 0.3–0.5 |
| Total anions (mEq) | about 130 to 170 | 137–151 |
| (5) chloride$^-$ | about 84 to 125 | 95–115 |
| (6) bicarbonate$^-$ | about 0 to 80 | 25–36 |
| (7) l-Lactate$^-$/pyruvate$^-$ | about 0 to 80 | 0–12 |
| (8) d-Betahydroxybutyrate$^-$/acetoacetate$^-$ | about 0 to 80 | 0–5 |
| (9) sum (6 + 7 + 8) | about 25 to 80 | 25–36 |
| Total nonionics | about 0 to 525 | 0.16–12 |
| (1) carbon dioxide | about 0 to 25 | 0.16–2 |
| (2) osmotically active material* | about 0 to 500 | 0–10 |
| Milliequivalent Ratio of Near-Equilibrium Couples | | |
| (10) ratio of HCO$_3^-$/CO$_2$ | about 0.1/1–55/0.1 | 17/1–33/0.16 |
| (11) ratio of l-lactate$^-$/pyruvate | about 20/1–1/1 | 10/1–5/1 |
| (12) ratio of d-$\beta$-Hydroxybutyrate$^-$/acetoacetate$^-$ | about 6/1–0.5/1 | 3/1–1.5/1 |
| (13) ratio of Na:Cl | about 1.24–1.55 | 1.24–1.50 |
| (14) osmolarity | about 260–765 | 280–315 |
| (15) pH | about 5–9 | 7.35–8.4 |

*An osmotically active material may be added in absence of ultrafiltration as a means of removing excess H$_2$O from patients in those set ups not equipped with newer pressure sustaining dialysis cartridges. At present, glucose is preferred.

As those skilled in the art will appreciate, when a physician desires to use any one or more of the near equilibrium couples as defined herein, then one can change the individual ratios at the discretion of the physician to achieve different chemical potentials. In the present illustrative examples, these ratios are set using the assumption of normal operating conditions.

The practice of the present invention is defined by the hereinabove presented equations. Those skilled in the art will readily understand that these equations alone set the practice of the present invention.

Shown in FIG. 7 is one embodiment of apparatus of the present invention with functional capability as previously indicated. Here concentrates are prepared and stored in vessels A, B ... N, as shown in FIG. 7. Each vessel A,B ... N is interconnected with a mixing chamber 100 by means of conduit means respectively designated as a, b ... n. In each conduit a,b ... n is functionally mounted a proportionating pump 101, 102, 103, 104, 105, etc.

A computer 110, or master control device, is interconnected with each of the proportionating pumps 101–105 so that each pump is actuatable and controllable by computer 110. A source (not detailed) of purified water input as labeled is provided and in the input line 115 is located a flow regulator 116 which is functionally inter-connected with the computer 110, as shown. Output past the flow regulator 116 in conduit 115 is input into an aerator 117 and in the aerator 117 inter mixing of carbon dioxide gas with the water is achieved so as to achieve dissolution of carbon dioxide in the water. A conventional aerator of the lung type is illustrated. Carbon dioxide is input past a gas feed regulator 120, the regulator 120 being functionally inter-connected with the computer 110 as shown; excess (undissolved) CO$_2$ is discharged. The water containing dissolved carbon dioxide exits through conduit 121 and passes through a flow regulator 122 which is functionally interconnected with the computer 110. Flow through conduit 121 proceeds into mixing chamber 100.

Thus, in mixing chamber 100 water containing a measured quantity of dissolved carbon dioxide is intermixed with individual ones of concentrates so as to produce an electrolyte solution wherein the exact composition of individual electrolyte components is controlled. The solution from mixture chamber 124 exits through conduit 124 and passes through a flow regulator 125, the regulator 125 being inter-connected functionally with the computer 110.

As those skilled in the art will appreciate, each regulator, such as regulator 125, can be provided with other devices besides a flow sensing and controlling means, such as heating means, pressure regulating means, safety devices of the usual sort employed in dialysis fluid delivery systems, and the like, all as is practiced conventionally in the art of dialysis fluid delivery systems.

From the flow regulator 125 in conduit 124, the fluid from mixing chamber 100 is fed to the dialyzer unit 130 which can be of conventional construction and here is preferably of the type which can be pressurized in the conventional prior art manner so as to achieve the processing effect in hemodialysis known as hyperfiltration to those skilled in the art.

To the dialyzer is fed in a counter-current flow manner as shown in FIG. 7 blood from the patient being dialyzed. Preparation treatment and control of blood flow is conventionally accomplished and does not constitute a part of the present invention.

From the dialyzer 130 spent dialysate is discharged through conduit 131 to waste.

As those skilled in the art will appreciate, the apparatus of FIG. 7 can be used to:
(a) prepare a hemodialysis fluid composition for treating an individual patient;
(b) prepare a hemodialysis composition which can be continuously varied in a desired (controlled) manner so as to achieve a predetermined rate of change of concentration of plasma electrolyte in the plasma of the patient whose blood is being hemodialyzed;
(c) practice a combination of (a) and (b).

Those skilled in the art will appreciate that the apparatus of FIG. 7 can also be used to prepare plasma concentrates, substitutes and the like by using appropriate concentrates for charging into the mixing chamber 100.

The mixing chamber 100, as will be appreciated, can incorporate more than one mixing device so as to assure that the output from mixing chamber 100 is uniform in composition and physical characteristics.

Various other configurations for the apparatus FIG. 7 can be utilized, as those skilled in the art will readily appreciate, to achieve the same or equivalent results.

EMBODIMENTS

The following examples are merely illustrative of the present invention and are not intended as a limitation upon the scope thereof.

EXAMPLES 1-8

Herewith in Table V below are compositional examples from the prior art illustrating the results obtaining from solving equation 2 so as to predict what the concentration of plasma electrolytes will be in the blood of a patient being returned to him from the dialysis machine assuming a normal human albumin concentration of 0.65 mM/l. The albumin charge changes depending upon the pH of the particular dialysis used being used. This latter point was not appreciated in the prior art since no attention was paid to the careful regulation pH nor was there any understanding as to why this regulation was important.

TABLE V

| | Prior Art Hemodialysis Fluids Containing 3–4 Cations. | | | | | | | |
|---|---|---|---|---|---|---|---|---|
| Example No. | | 1 | | 2 | | 3 | | 4 |
| Units | | 5 a 1 | | 5 d 1 | | 5 a 1 | | 5 a 3 |
| mmoles | Normal Plasma N.E.J.M. 283, 1285 1970 | Kolff 1947 | Est. Return Plasma alb. = 0.65 mM | Brigham 1952 | Est. Return Plasma alb. = 0.65 mM | Scribner's Acetate 1964 | Est. Return Plasma alb. = 0.65 mM | Usual Commercial Acetate 1981 | Est. Return Plasma alb. = 0.65 mM |
| $Na^+$ | 136–145 | 126 | 126.98 | 140 | 137.13 | 135 | 128.1 | 140 | 133.9 |
| $K^+$ | 3.5–5.0 | 5.6 | 5.64 | 4 | 3.92 | 1.5 | 1.42 | 2 | 1.91 |
| $Ca^+$ | 2.1–2.6 | 1.0 | | 1.25 | | 1.25 | | 0.875 | |
| free $[Ca^{2+}]$ | [1.06] | | [1.09] | | [1.28] | | [1.20] | | [0.86] |
| $Mg^{2+}$ | 0.75–1.25 | — | | 0.5 | | 0.5 | | 0.375 | |
| free $[Mg^{2+}]$ | [0.53] | | | | [0.51] | | [0.43] | | [0.37] |
| Σ mEq Cations | 142.7–153.2 | 133.6 | 134.9 | 147.5 | 144.63 | 140 | 132.83 | 144.5 | 137.0 |
| $Cl^-$ | 100–106 | 109 | 94.56 | 120.7 | 107.72 | 105 | 96.7 | 106 | 96.9 |
| $HCO_3^-$ | 26–28 | 23.9 | 20.73 | 26.8 | 23.92 | | | | |
| Σ Pi | 1–1.45 | | | | | | | | |
| Charge on Albumin | | (−30) | (−19.5) | (−20) | (−13.0) | (−6) | (−3.9) | (−6) | (−3.9) |
| L-lactate$^-$ | 0.6–1.8 | | | | | | | | |
| pyruvate$^-$ | | | | | | | | | |
| Lact/pyr | | | | | | | | | |
| D-βOHbutyrate$^-$ | | | | | | | | | |
| acetoacetate$^-$ | | | | | | | | | |
| β HB/acac | | | | | | | | | |
| acetate$^-$ | | | | | | | 35 | 32.5 | 38.5 | 36.2 |
| Other | | | | | | | | | |
| Σ mEq anions | 128.7–139.4 | 132.9 | 134.8 | 147.5 | 144.64 | 140 | 133.10 | 144.5 | 137.6 |
| $Na^+/Cl^-$ | 1.28–1.45 | 1.16 | 1.34 | 1.16 | 1.27 | 1.29 | 1.32 | 1.32 | 1.38 |
| Glucose or others | 3.9–5.6 | 76–151 | 76–151 | 10 | 10–? | — | — | — | — |
| $CO_2$ | 0.99–1.39 | 0 | 0 | 1.24 | 1.24 | — | — | — | — |
| pH | 7.35–7.45 | ≈8.6 | ≈8.6 | 7.4 | 7.3 | ≈5.5–6.5 | ≈5.5–6.5 | ≈5.5–6.5 | ≈5.5–6.5 |
| Σ mOsm | 285–295 | 343–418 | 340–418 | 304.8 | 278.48 | 278.25 | 260.4 | 287.75 | 270.1 |
| Example No. | | 5 | | 6 | | 7 | | 8 |
| Units | | 5 a 4 | | 5 a 5 | | 5 b 2 | | 5 b 3 |
| mmoles | Normal Plasma N.E.J.M. 283, 1285 1970 | Bjaelder "Low" Acetate | Est. Return Plasma alb. = 0.65 mM | Bjaelder "High" Acetate | Est. Return Plasma alb. = 0.65 mM | COBE $HCO_3^-$/ HAcetate | Est. Return Plasma alb. = 0.65 mM | Kraut $HCO_3^-$/ HAcetate | Est. Return Plasma alb. = 0.65 mM |
| $Na^+$ | 136–145 | 134 | 129.03 | 136 | 131.53 | 135 | 132.85 | 140 | 135.6 |
| $K^+$ | 3.5–5.0 | 2.2 | 2.12 | 2.2 | 2.13 | 2 | 1.97 | 2 | 1.97 |
| $Ca^+$ | 2.1–2.6 | 1.84 | | 1.91 | | 1.5 | | 1.75 | |
| free $[Ca^{2+}]$ | [1.06] | | [1.52] | | [1.91] | | [1.55] | | [1.76] |
| $Mg^{2+}$ | 0.75–1.25 | | | | | 0.375 | | | |
| free $[Mg^{2+}]$ | [0.53] | | | | | | [0.39] | | |

TABLE V-continued

| | | | | Prior Art Hemodialysis Fluids Containing 3-4 Cations. | | | | | |
|---|---|---|---|---|---|---|---|---|---|
| Σ mEq Cations | 142.7–153.2 | 139.88 | 134.79 | 142.02 | 137.48 | 140.75 | 138.75 | 145.5 | 141.1 |
| Cl$^-$ | 100–106 | 107.28 | 97.4 | 103.82 | 93.85 | 106.5 | 94.6 | 107 | 96.5 |
| HCO$_3^-$ | 26–28 | — | — | — | — | 33 | 29.3 | 33 | 29.5 |
| Σ Pi | 1–1.45 | | | | | | | | |
| Charge on Albumin | | (−12) | (−7.8) | (−14) | (−9.1) | (−20) | (−13) | (−20) | (−13) |
| L-lactate$^-$ | 0.6–1.8 | | | | | | | | |
| pyruvate$^-$ | | | | | | | | | |
| Lact/pyr | | | | | | | | | |
| D-βOHbutyrate$^-$ | | | | | | | | | |
| acetoacetate$^-$ | | | | | | | | | |
| β HB/acac | | | | | | | | | |
| acetate$^-$ | | 32.6 | 29.6 | 38.2 | 34.5 | HAc 2 | 1.78 | HAc 2 | 1.8 |
| Other | | | | | | | | ?3.5 | |
| | | | | | | | | Gluconate | |
| Σ mEq anions | 128.7–139.4 | 139.88 | 134.8 | 142.02 | 137.48 | 141.5 | 125.68 | 145.5 | 128 |
| Na$^+$/Cl$^-$ | 1.28–1.45 | 1.25 | 1.32 | 1.31 | 1.40 | 1.27 | 1.40 | 1.31 | 1.4 |
| Glucose | 3.9–5.6 | | | | | | | | |
| or others | | | | | | | | | |
| CO$_2$ | 0.99–1.39 | | | | | ≈1.5 | ≈1.5 | ≈1.5 | ≈1.5 |
| pH | 7.35–7.45 | ≈6.5 | ≈6.5 | ≈6.7 | ≈6.7 | ≈7.4 | ≈7.4 | ≈7.4 | ≈7.4 |
| Σ mOsm | 285–295 | 277.92 | 259.97 | 282.13 | 263.95 | 280.4 | 262.44 | 289.3 | 267 |

5 a 1 Kolff W J. New Ways of Treating Uremia. J&A Churchill, London, 1974. Early hemodialysis.
5 d 1 Murphy W P, Swan R C, Walter C, Weller J M, Merrill J P. J Lab Clin Med 40: 436, 1952. Essentially Krebs Henseleit, but with lower Mg and Ca.
5 a 2 Mion C M, Hegstrom R M, Boen S T, Scribner B H. Trans Am Soc Artif intern Organs 10: 110-113, 1964. "Solved" the excess Cl$^-$ problem and avoided the precipitation of Ca and Mg with bicarbonate solutions. Ultrafiltration removed the excess H$_2$O. The amount of pressure required is given by the Van't Hoff eqn VI.
5 a 3 Parsons F M, Stewart W K. The composition of dialysis fluid. In: Druckker W, Parsons F M, Maher J F, eds. Replacement of Renal Function by Dialysis, 2nd Edition, 1984, Martinus Nijhoff: Hingham, 148-170. The range of cations and acetate used is given in this article.
5 a 4 Bjaelder et al. Nephron 27: 142-145, 1981. The hemodialysis patients remain acidotic on "low acetate" fluid. This fluid violates the "safe entry" concept, leaving the patient chronically hyperphosphatemic, and should be forbidden.
5 a 5 Bjaelder et al. Nephron 27: 142-145, 1981. While "curing" the chronic acidosis, note the higher Na:Cl ratio in 5a5 compared to 5a4. This difference was not noted by Bjaelder. This fluid also leaves the patient hyperphosphotemic, and should also be forbidden.
5 b 2 Commercial Fluid; COBE, 1201 Oak St. Lakewood CO. Uses acetic acid to generate CO$_2$, and thus risks acetate toxicity.
5 b 3 Kraut J, Gafter U, Brautbar N, Miller J, Shinaberger J. Clin Nephrol 15: 181-184, 1981.

EXAMPLES 9 THROUGH 19

Herewith in Table IV are given specific new fluids which are each formulated to treat one of the seven commonly used indications for hemodialysis, as follows:

1. chronic uremia (otherwise healthy)
2. chronic uremia (with hypertension)
3. chronic uremia (with cerebral vascular insufficiency)
4. uremia with diabetes
  (a) controlled
  (b) moderate ketoacidosis
  (c) severe ketoacidosis and dehydration
5. volume overload
6. poisoning
7. hyperkalemia Initial plasma electrolytes are given simulating the clinical conditions described. A dialysis fluid is created from equation 2 to achieve the final plasma electrolytes concentrations desired in the treatment of the condition.

TABLE VI

| | | | Values are in m moles/L fluid | | | | | | | |
|---|---|---|---|---|---|---|---|---|---|---|
| | | | | | | Normal Plasma Values | | | | |
| Example No. | Condition & Symptoms | Intial Rx Final | 136–145 Na+ | 3.5–5.0 K+ | 2.1–2.6 [1.065] Ca2+ | 0.75–1.25 [0.53] Mg2+ | 100–106 Cl− | 26–28 HCO$_3$− | 1–1.45 ΣPi | 2.9–8.5 BUN |
| | I Chronic Uremia | | | | | | | | | |
| | A. Otherwise Healthy | | | | | | | | | |
| (9) | 1 Klooster's Minimal with CO$_2$ | Intial Plasma | 122–130 | 5.5–6 | 2.0–2.3 | 1.2–1.5 | 100 | 15–17 | 1.5–3.0 | 25–36 |
| | | Dial. Fluid | 138.77 | 3.06 | 1.46 | 0.49 | 112.1 | 33.63 | — | — |
| | | Final Plasma | 136.00 | 3.00 | [1.50] | [0.50] | 100 | 30 | — | (9) |
| (10) | 2 Klooster-Krebs Compromise with Lac/Pyr no add CO$_2$ but 1-lactic acid makes CO$_2$ from HCO$_3^-$ | Dial. Fluid | 135.50 | 2.0 | [1.50] | [0.38] | 106.5 | 33 | — | — |
| | | Final Plasma | 133.31 | 1.97 | [1.55] | [0.39] | 94.6 | 29.32 | — | (9) |
| (11) | 3 Krebs-Ketone with Redox Control plus CO$_2$ | Dial. Fluid | 138.77 | 3.06 | 1.46 | 0.49 | 104.25 | 32.51 | — | — |
| | | Final Plasma | 135.99 | 3.00 | [1.50] | [0.50] | 93.00 | 29.00 | — | (9) |
| (12) | B. Chronic Uremia with Hypertension Low Na, High Mg, Low Ca. | Intial Plasma | 125–130 | 5.5–6.0 | 1.8–2.3 | 1.1–1.4 | 95–100 | 17–20 | 1.5–3.0 | 25–36 |
| | | Dial. Fluid | 132.33 | 2.85 | [1.21] | [0.51] | 97.05 | 32.59 | — | — |
| | | Final Plasma | 130 | 2.8 | [1.25] | [0.53] | 86.96 | 29.00 | — | (9) |
| (13) | C. Chronic Uremia with Cerebro-Vascular Insufficiency Higher Na add Glucose | Intial Plasma | 128–132 | 5.5–6.5 | 1.8–2.3 | 1.1–1.4 | 95–100 | 15–17 | 1.5–3.0 | 25–36 |
| | | Dial Fluid | 143.04 | 3.07 | 1.46 | 0.49 | 114.75 | 32.47 | — | — |
| | | Final Plasma | 140 | 3.0 | [1.50] | [0.50] | 102.5 | 29 | — | (9) |
| | D. Uremia plus Diabetes | | | | | | | | | |
| (14) | 1 Controlled | Intial Plasma | 130 | 5.8 | 2.0 | 1.2 | 106 | 17 | 1.5–3.0 | 25–36 |
| | | Dial. Fluid | 137.69 | 2.86 | 1.46 | 0.49 | 111.92 | 32.52 | — | — |
| | | Final Plasma | 135 | 2.8 | [1.50] | [0.50] | 99.8 | 29 | — | (9) |

TABLE VI-continued

| | | | | | | | | | | | |
|---|---|---|---|---|---|---|---|---|---|---|---|
| (15) | 2 With Moderate | Intial Plasma | 130 | 5.8 | 2.0 | 1.2 | 106 | 17 | 1.5–3.0 | 25–36 | |
| | Ketoacidosis | Dial Fluid | 137.74 | 3.06 | 1.46 | 0.49 | 110.09 | 32.51 | 1.07 | — | |
| | with Pi | Final Plasma | 135 | 3.0 | [1.5] | [0.50] | 98.2 | 29 | 1.0 | (9) | |
| (16) | 3 Diabetes with | Intial Plasma | 145 | 7 | 2 | 0.8 | 114 | 2 | 4 | 25–36 | |
| | Severe Ketoacido- | Dial. Fluid | 143.06 | 3.58 | 1.01 | 0.59 | 115.26 | 32.46 | 1.16 | — | |
| | sis & Dehydration | Final Plasma | 140 | 3.5 | [1.03] | [0.6] | 102.96 | 29 | 1 | (9) | |
| (17) | E. Volume Overload with | Initial Plasma | 120 | 4.8 | 2.3 | 0.7 | 90 | 24 | 1 | 70 | |
| | or without cardiac failure | Dial. Fluid | 135.64 | 3.6 | 0.97 | 0.50 | 107.01 | 33.02 | 1.20 | — | |
| | dialysis with maximum ultra- | Final Plasma | 135 | 3.58 | [1.03] | [0.53] | 94 | 29 | 1.0 | (9) | |
| | filtration of 200–250 mm Hg | | | | | | | | | | |
| | II Non-uremic Conditions | | | | | | | | | | |
| (18) | F. Poisioning | Initial Plasma | 138 | 4.0 | 2.4 | 1.0 | 103 | 23 | 1.2 | 10 | |
| | | Dial. Fluid | 143.16 | 4.09 | 1.47 | 0.68 | 116.38 | 30 | 1.39 | — | |
| | | Final Plasma | 140 | 4.0 | [1.50] | [0.70] | 104.04 | 27 | 1.2 | — | |
| (19) | G. Life Threatening | Initial Plasma | 138 | 7.0 | 2.1 | 0.9 | 100 | 25 | 3 | 70 | |
| | Hyperkalemia | Dial. Fluid | 138.7 | 0 | 1.46 | 0.68 | 103.96 | 37.01 | 1.17 | — | |
| | (given with insulin, be ready to | Final Plasma | 136 | 0 | [1.5] | [0.7] | 92.6 | 33 | 1 | — | |
| | add $K^+$ when crisis passes.) | | | | | | | | | | |

Values are in m moles/L fluid

Normal Plasma Values Charge on Conc. of

| Ex-am-ple No. | | 1-Lact/ Pyr 0.5–5/ 0.05–0.25 | $d\beta HB$/ Acac 0.015–8/ 0.01–1.6 | Albumin −20/ mole @ pH 7.4 | Albu-min 0.5–0.75 | $CO_2$ 1.27–1.79 | pH 7.31–7.42 | Glu-cose 3.9–6.7 | $Na^+/Cl^-$ 1.28–1.45 | Σ cations mEq/L 142–153 | Σ anions mEq/L 129–139 |
|---|---|---|---|---|---|---|---|---|---|---|---|
| | I Chronic Uremia | | | | | | | | | | |
| | A. Otherwise Healthy | | | | | | | | | | |
| | Initial Plasma | — | — | −20 | 0.65 | ≈0.96 | 7.35 | 7 | 1.2–1.3 | | |
| (9) | 1 Dial. Fluid (Minimal) | — | — | — | — | 1.54 | 7.44 | — | 1.26 | | |
| | Final Plasma | — | — | −20 | 0.65 | 1.44 | 7.42 | — | 1.36 | | |
| (10) | 2 Dial Fluid (K, K Compromise- no added $CO_2$) | 2/0.5 | — | — | — | " | " | — | 1.27 | | |
| | Final Plasma | 1.78/0.44 | — | −20 | 0.65 | " | ≈7.4 | — | 1.41 | | |
| (11) | 3 Dial Fluid (K-K with Redox Control + $CO_2$) | 1.79/0.45 | 5.04/1.68 | — | — | 1.48 | 7.44 | | 1.33 | | |
| | Final Plasma | 1.60/0.40 | 4.5/1.5 | −20 | 0.65 | 1.38 | 7.42 | | 1.46 | | |
| (12) | Uremia with Hypertension | | | | | | | | | | |
| | Initial Plasma | " | " | −20 | 0.65 | " | 7.35 | | 1.25–1.37 | | |
| | Dial. Fluid | 2.7/0.67 | 4.21/1.40 | — | — | 1.45 | 7.44 | | 1.36 | | |
| | Final Plasma | 2.5/0.5 | 4/1 | −20 | 0.65 | 1.39 | 7.42 | | 1.49 | | |
| (13) | C. Uremia with Cerebrovascular Insufficiency | | | | | | | | | | |
| | Initial Plasma | " | " | −20 | 0.65 | "0.96 | 7.35 | | 1.28–1.39 | | |
| | Dial. Fluid | 1.12/0.28 | 1.05/0.35 | — | — | 1.48 | 7.44 | 10 | 1.27 | 150 | 150 |
| | Final Plasma | 1/0.25 | 1/0.25 | −20 | 0.65 | 1.38 | 7.42 | 9.4 | 1.37 | | |
| | D. Uremia plus Diabetes | | | | | | | | | | |
| (14) | 1 Controlled Initial | " | 1.5/0.5 | −20 | 0.65 | | " | 10–20 | 1.23 | | |
| | Dial. Fluid | — | — | — | — | 1.48 | 7.44 | 10 | 1.23 | | |
| | Final Plasma | — | — | −20 | 0.65 | 1.38 | 7.42 | 10 | 1.37 | | |
| (15) | 2 With Moderate Ketoacidosis | | | | | | | | | | |
| | Initial Plasma | — | Σ4–6 | | 0.65 | | 7.28 | 20–30 | 1.22 | | |
| | Dial. Fluid | — | — | — | — | 1.48 | 7.44 | 10 | 1.25 | | |
| | Final Plasma | — | — | −20 | 0.65 | 1.38 | 7.42 | 10 | 1.37 | | |
| (16) | Diabetes with Ketoacidosis | | | | | | | | | | |
| | Initial Plasma | 3.8/0.2 | 17/3 | −9 | 0.65 | ≈0 | 7.02 | 50 | 1.27 | 155 | 155 |
| | Dial. Fluid | — | — | — | — | 1.48 | 7.44 | 10 | 1.24 | | |
| | Final Plasma | — | — | −20 | 0.65 | 1.38 | 7.42 | 10 | 1.36 | 146.76 | 146.76 |
| (17) | E. Volume Overload | | | | | | | | | | |
| | Initial Plasma | — | — | −16 | 0.65 | 1.23 | 7.30 | 7 | 127.8 | | |
| | Dial. Fluid | — | — | — | — | 1.51 | 7.43 | — | 1.27 | | |
| | Final Plasma | — | — | −20 | 0.845 | 1.48 | 7.42 | — | 1.44 | 141.7 | 141.7 |
| | II Non-uremic Conditions | | | | | | | | | | |
| (18) | F. Poisioning | | | | | | | | | | |
| | Initial Plasma | " | " | −20 | 0.65 | " | 7.35 | 5 | 1.34 | | |
| | Dial. Fluid | 1.97/0.47 | — | — | — | 1.40 | 7.44 | 10 | 1.23 | | |
| | Final Plasma | 1.86/0.44 | — | −20 | 0.65 | 1.29 | 7.42 | 10 | 1.35 | 148.4 | 148.4 |
| (19) | G. Hyperkalemia | | | | | | | | | | |
| | Initial Plasma | | | −20 | 0.65 | | 7.30 | — | 1.38 | | |
| | Dial. Fluid | — | — | — | — | 1.33 | 7.5 | 10 | 1.34 | | |
| | Final Plasma | — | — | −20 | 0.65 | 1.47 | 7.48 | 10–15 | 1.47 | | |

EXAMPLE 20

An example illustrating the linearization of the rate of urea removal from a patient with renal failure so as to decrease the rapid osmotic shifts inherent in current (prior art) practice. Such osmotic shifts are thought to play a role in the nausea, headache and general malaise known as the disequilibrium syndrome.

Medical History and Problem

A 70 year old otherwise healthy woman with chronic renal failure from polycystic kidney disease is brought in three days after routine hemodialysis with 38 mM acetate. During previous dialysis, the patient suffered from intense headache, nausea and vomiting particularly during the initial portions of the 4 hour dialysis session. Following dialysis, she complained of weakness and tiredness for the remainder of the next day, feeling relatively well only on the day she was scheduled to return for her next dialysis.

METHODS

It is decided to switch from acetate dialysis to minimal dialysis media given in example 9 to avoid the problems inherent in acetate dialysis. To attempt to lessen the "disequilibrium syndrome" it is decided that the woman will be dialyzed until her BUN is reduced to 10 mM from the 30 mM she has 3 days after each dialysis Using the apparatus described here two minimal dialysis media are prepared The first contains 25 mM urea and the second 0 mM urea. The woman undergoes usual dialysis starting with a solution containing 25 mM urea mixing with the 0 in M urea minimal media to form a linear gradient instead of a hyperbolic one. The final dialysis solution contains no urea and is the solution given to the patient during the last portion of dialysis.

RESULTS

The blood of the patient is sampled during dialysis and it is noticed that the blood urea drops at a roughly constant rate during dialysis ending at about 10 mM at four hours.

It is further observed that the patient does not suffer nausea, headache and vomiting during this dialysis session. Further the removal of acetate eliminates the hypotension the patient previously experienced as well as the "tiredness" lasting the next two days.

Other and further aims, objects, purposes, advantages, uses, and the like for the present invention will be apparent to those skilled in the art from the present specification. The problems in acetate dialysis, including pyrophosphate and calcium build-up in liver, post-dialysis hyperphosphatemia and hyperparathyroidism are avoided. Likewise, the abnormal redox state with diminished $[\Sigma ATP]/[\Sigma ADP][\Sigma Pi]$ ratio seen with dialysis with L-lactate alone are eliminated.

I claim:

1. In a process for dialyzing through a dialysis membrane a dialyzable fluid which has dispersed and/or dissolved therein a nonpermanent charged material the improvement of which comprises controlling the ionic composition of said dialyzable fluid by regulating during the dialyzing process the ionic composition of the dialyzing fluid being used for dialyzing said dialyzable fluid by varying the concentration ratios one to another between permeant cations and/or permeant anions of the dialyzing fluid to determine the relative concentrations of permeant ions in said dialyzable fluid.

2. The process of claim 1 wherein the charge of said nonpermanent charged material in said dialyzable fluid is regulated by varying at least one of the following:
   (a) the pH of said dialyzing fluid,
   (b) the temperature of said dialyzing fluid,
   (c) the ionic strength of said dialyzing fluid,
   (d) the concentration of polyvalent cations present in said dialyzing fluid, and
   (e) the relative concentration of permeant materials one to the other in said dialyzable fluid, said permeant materials being bindable to said nonpermanent charged material in such a way as to vary the charge associated with said nonpermanent charged material.

3. The process of claim 1 wherein said dialyzable fluid comprises blood of a mammal and the charge associated with said nonpermanent charged material in said blood is regulated by:
   (a) varying the pH of said dialyzing fluid, or
   (b) varying the of permeant ions in said dialyzing fluid which specifically interact with said nonpermanent charged material, or
   (c) varying both (a) and (b), and said dialyzing fluid contains dissolved therein at least one of the permeant ionic materials found in said blood.

4. In a hemodialysis process wherein a dialyzing solution is used to hemodialyze a mammalian blood through a dialysis membrane, the improvements of which comprises the steps of:
   (A) preparing a starting dialyzing solution comprising water which has dissolved therein components generically characterized as follows:

| Component | Quantity range in mmoles per liter |
|---|---|
| total cations (mEg/L) | about 130 to 170 |
| (a) sodium$^{1+}$ | about 130 to 155 |
| (b) potassium$^{1+}$ | about 0 to 6 |
| (c) calcium$^{2+}$ | about 0 to 3 |
| (d) magnesium$^{2+}$ | about 0 to 2 |
| total anions (mEq/L) | about 130 to 170 |
| (e) chloride$^{1-}$ | about 84 to 125 |
| (f) bicarbonate$^{1-}$ | about 0 to 80 |
| (g) L-lactate$^{1-}$/pyruvate$^{1-}$ | about 0 to 80 |
| (h) D-$\beta$ hydroxybutyrate$^{1-}$/acetoacetate | about 0 to 80 |
| (i) sum (f + g + h) | about 25 to 80 |
| total nonionics | about 0 to 525 |
| (j) carbon dioxide | about 0 to 25 |
| (k) osmotically active materials | about 0 to 500 |
| millequivalent ratios of near equilibrium couples (if present) | |
| (l) bicarbonate:CO$_2$ | about 0.1/1 to 55/0.1 |
| (m) L-lactate:pyruvate | about 20/1 to 1/1 |
| (n) D-$\beta$ hydroxybutyrate:acetoacetate | about 6/1 to 0.5/1 |
| (o) sodium:chloride | about 1.24 to 1.55 |
| milliosmolarity | about 260 to 765 |
| pH | about 5 to 9 |

(B) commencing said hemodialysis of said blood using said starting dialyzing solution,
   (C) changing the concentration ratio of at least two selected anions relative to one another in said starting dialyzing solution during the dialyzing procedure, thereby also simultaneously altering the concentration ratio of each of said selected anions to each of the remaining respective anions present in said starting dialyzing solution, thereby producing a resulting dialyzing solution, said resulting dialyzing solution comprising water which has dissolved therein components as generically above characterized, and
   (D) continuing said hemodialysis of said blood using said resulting dialyzing composition while said changing is occurring.

5. The process of claim 4 wherein said changing is carried out at a selected rate with respect to time until a predetermined final concentration ratio of said selected anions is achieved.

6. The process of claim 4 wherein said changing is carried out using at least two geometrically configured, functionally interconnected, subcombination solution supply vessels whose respective effluents when combined in admixture produce the desired said resulting solution.

7. The process of claim 4 wherein said changing is carried out using water and a plurality of preliminarily prepared subcombination concentrates each of which is charged in a regulated quantity to a mixing zone, thereby to produce said resulting dialyzing solution.

8. In a hemodialysis process wherein a dialyzing solution is used to hemodialyze a mammalian blood through a dialysis membrane, the improvement of which comprises the steps of:

(A) preparing a plurality of staring materials, each said material, comprising a preselected subcombination of components desired in a dialyzing solution comprising water which has dissolved therein components generically characterized as follows:

| Component | Quantity range in mmoles per liter |
|---|---|
| total cations (mEg/L) | about 130 to 170 |
| (a) sodium$^{1+}$ | about 130 to 155 |
| (b) potassium$^{1+}$ | about 0 to 6 |
| (c) calcium$^{2+}$ | about 0 to 3 |
| (d) magnesium$^{2+}$ | about 0 to 2 |
| total anions (mEq/L) | about 130 to 170 |
| (e) chloride$^{1-}$ | about 84 to 125 |
| (f) bicarbonate$^{1-}$ | about 0 to 80 |
| (g) L-lactate$^{1-}$/pyruvate$^{1-}$ | about 0 to 80 |
| (h) D-$\beta$ hydroxybutyrate$^{1-}$/ acetoacetate | about 0 to 80 |
| (i) sum (f + g + h) | about 25 to 80 |
| total nonionics | about 0 to 525 |
| (j) carbon dioxide | about 0 to 25 |
| (k) osmotically active materials | about 0 to 500 |
| milliequivalent ratios of near equilibrium couples (if present) | |
| (l) bicarbonate:CO$_2$ | about 0.1/1 to 55/0.1 |
| (m) L-lactate:pyruvate | about 20/1 to 1/1 |
| (n) D-$\beta$ hydroxybutyrate:acetoacetate | about 6/1 to 0.5/1 |
| (o) sodium:chloride | about 1.24 to 1.55 |
| milliosmolarity | about 260 to 765 |
| pH | about 5 to 9 |

(B) charging each of said starting components and optionally water to a mixing zone while simultaneously and separately regulating the instantaneous flow rate at which each respective said components enters said mixing zone thereby providing a desired resulting dialyzing solution having a predetermined composition at any given time, said composition being within said generic characterization, (C) moving said resulting dialyzing solution from said mixing zone over one side of said dialysis membrane while passing said blood over the opposed side of said dialysis membrane, thereby hemodialyzing said blood with said dialyzing solution, and (D) changing each one of a plurality of said respective instantaneous flow rates in a predetermined manner during both said charging and said moving, whereby the concentration ratio of at least one selected anions of said dialyzing solution changes one to the other from an initial predetermined formulation to a final predetermined formulation during said hemodialysis procedure.

9. The procedure of claim 8 wherein a plurality of said starting solutions are each a concentrate relative to the amount of solute material therein which is present in said resulting dialyzing solution.

10. The procedure of claim 9 wherein said changing is carried out using a combination of computer controlled adjustable valves and pump means, there being a different one of such valves functionally associated with each one of said concentrate starting solutions and said water, and wherein said computer is programmed to achieve each of said respective flow rates in said predetermined manner.

11. The procedure of claim 8 wherein said changing is carried out using at least two geometrically configured, functionally interconnected subcombination supply vessels whose respective effluents when combined in admixture produce said resulting dialyzing solution.

12. The procedure of claim 8 wherein the rate of change corresponds to a linear rate equation.

13. The procedure of claim 8 wherein the rate of change is generally continuous and extends over a time interval which is sufficient for the initial concentration of blood electrolytes present in the plasma of said blood to change to a value which is about halfway between the anticipated final concentration of said blood electrolytes present in said plasma at the termination of said hemodialysis and the initial concentration of said blood electrolytes, and such time interval is about one half the total time interval anticipated for the duration of said hemodialysis procedure.

14. In a hemodialysis apparatus of the type which moves dialyzing solution over one face of a dialysis membrane while mammalian blood is passed over the opposed face of such membrane, the improvement which comprises the combination:

(A) a plurality of reservoir means, each one of which is adapted to supply a different starting subcombination of components such that when such component subcombinations are mixed together in predetermined proportions, a desired such dialyzing solution results, (B) conduit means interconnecting said reservoir means in a predetermined pattern and including a dialyzing solution mixing chamber means, (C) means for regulating the individual output of each component subcombination from its respective means to said mixing chamber means to produce a desired such dialyzing solution and to change the concentration ratio of at least two of the cation and/or anion components in such dialyzing solution one to the other from an initial predetermined value to a final predetermined value within a predetermined dialysis time interval, (D) solution delivery means for moving said desired dialyzing solution from said mixing chamber means over said one face of said dialysis membrane; and (E) blood delivery means for moving said blood over said opposed face of said dialysis membrane.

15. In a hemodialysis apparatus of the type which hemodialysis fluid over one face of a dialysis membrane while mammalian blood is passed over the opposed face of such membrane, the improvement which comprises in combination:

(a) is plurality of reservoir means, each one of which is adapted to hold a different starting subcombination of components such that said component subcombination when admixed together in predetermined proportions comprises a desired dialyzing solution (b) a mixing chamber means, (c) a different variable valve means functionally associated with each one of said reservoir means, (d) conduit means connecting each of said valve means with said mixing chamber means, (e) means for pressurizing each of said reservoir means to a predetermined extent, (f) programmable computer means functionally associated with each of said valve means, said computer being adapted to regulate individually the rate of flow of each of said component subcombination from its associated said reservoir means into said mixing chamber means at a predetermined value to change the concentration ratio one to the other of at least two of the cations and/or anions dissolved in said dialyzing solution from an initial predetermined value to a final predetermined value within a predetermined dialysis time interval, (g) dialysis solution delivery means for moving fluid from said mixing chamber means over said one face of said dialysis membrane, and (h) blood delivery means for moving said blood over said opposed face of said dialysis membrane.

16. In a hemodialysis separable apparatus of the type which moves dialyzing solution over one face of a dialysis membrane while mammalian blood is passed over the opposed face of such membrane, during dialysis, the improvement which comprises in combination:

(a) a series of at least two individually geometrically configured, gradient making reservoir means, each one of which is adapted to hold a different starting subcombination solution having ion components such that said solution subcombinations when admixed together in predetermined proportions comprise a desired dialyzing solution, said reservoir means including cooperating means interconnecting respective ones of said reservoir means causing the respective such solution in each one of said reservoir means to successively flow therefrom at a predetermined rate into a preselected another one of said reservoir means in said series, providing a desired said dialyzing solution with the concentration ratio one to the other of at least two of the components of such dialyzing solution changing from an initial predetermined value to a different final predetermined value within a predetermined time interval, during said dialysis;

(b) solution delivery means for moving said desired dialyzing solution over said one face of said dialysis membrane, and (c) blood delivery means for moving said blood over said opposed face of said dialysis membrane.

* * * * *